US011332763B2

(12) United States Patent
Singh et al.

(10) Patent No.: US 11,332,763 B2
(45) Date of Patent: May 17, 2022

(54) MUTANT MICROORGANISMS AND METHODS OF MAKING AND USING

(71) Applicant: NUtech Ventures, Lincoln, NE (US)

(72) Inventors: Raghuveer Singh, Lincoln, NE (US); Derrick White, Lincoln, NE (US); Paul Blum, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/568,347

(22) PCT Filed: Apr. 21, 2016

(86) PCT No.: PCT/US2016/028647
§ 371 (c)(1),
(2) Date: Oct. 20, 2017

(87) PCT Pub. No.: WO2016/172341
PCT Pub. Date: Oct. 27, 2016

(65) Prior Publication Data
US 2018/0100168 A1    Apr. 12, 2018

Related U.S. Application Data

(60) Provisional application No. 62/150,345, filed on Apr. 21, 2015.

(51) Int. Cl.
| | |
|---|---|
| *C12P 7/06* | (2006.01) |
| *C12P 3/00* | (2006.01) |
| *C12N 1/36* | (2006.01) |
| *C12N 9/04* | (2006.01) |
| *C12N 9/12* | (2006.01) |
| *C12N 9/88* | (2006.01) |
| *C12P 7/44* | (2006.01) |
| *C12P 7/54* | (2006.01) |
| *C12N 1/18* | (2006.01) |
| *C12N 1/20* | (2006.01) |
| *C12R 1/15* | (2006.01) |
| *C12R 1/145* | (2006.01) |
| *C12R 1/865* | (2006.01) |

(52) U.S. Cl.
CPC .............. *C12P 7/065* (2013.01); *C12N 1/185* (2021.05); *C12N 1/205* (2021.05); *C12N 1/36* (2013.01); *C12N 9/0006* (2013.01); *C12N 9/1217* (2013.01); *C12N 9/88* (2013.01); *C12P 3/00* (2013.01); *C12P 7/44* (2013.01); *C12P 7/54* (2013.01); *C12Y 101/01027* (2013.01); *C12Y 207/02001* (2013.01); *C12Y 401/0103* (2013.01); *C12Y 401/01039* (2013.01); *C12R 2001/145* (2021.05); *C12R 2001/15* (2021.05); *C12R 2001/865* (2021.05); *Y02E 50/10* (2013.01)

(58) Field of Classification Search
None
See application file for complete search history.

(56) References Cited

U.S. PATENT DOCUMENTS

| | | | |
|---|---|---|---|
| 2009/0155869 A1* | 6/2009 | Buelter | C12N 15/52 435/160 |
| 2009/0215130 A1 | 8/2009 | Iyo et al. | |
| 2012/0094343 A1* | 4/2012 | Hogsett | C12N 9/0006 435/139 |
| 2014/0087436 A1 | 3/2014 | Tabita et al. | |

OTHER PUBLICATIONS

Yoshikuni et al. Curr Opin Chem Biol. Apr. 2007;11(2):233-9. Epub Mar. 13, 2007 (Year: 2007).*
Nanavati et al. Appl Environ Microbiol. Feb. 2006;72(2):1336-45. (Year: 2006).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Archer, "Uncoupling of methanogenesis from growth of *Methanosarcina barkeri* by phosphate limitation," Appl Environ Microbiol, 1985 50(5):1233-7.
Blum et al., "Cloning and in vivo and in vitro regulation of cyclic AMP-dependent carbon starvation genes from *Escherichia coli*," J. Bacteriol, Jul. 1990, 172(7):3813-20.
Blum et al., "Gene replacement and retrieval with recombinant M13mp bacteriophages," J. Bacteriol., Jan. 1989,171:538 546.
Boucher and Noll, "Ligands of thermophilic ABC transporters encoded in a newly sequenced genomic region of *Thermotoga maritima* MSB8 screened by differential scanning fluorimetry," Appl. Environ. Microbiol., 2011, 77:6395-9.
Bzymek and Lovett, "Instability of repetitive DNA sequences: the role of replication in multiple mechanisms," PNAS, 2001, 98:8319-25.
Cha et al., "Metabolic engineering of *Caldicellulosiruptor bescii* yields increased hydrogen production from lignocellulosic biomass," 2013, Biotechnology for Biofuels, 2013, 6: 85.
Chung et al., "Direct conversion of plant biomass to ethanol by engineered *Caldicellulosiruptor bescii*," PNAS, 2014, 111: 8931-8936.
Dwidar et al., "The future of butyric acid in industry," The Scientific World Journal, 2012, 471417.
Frascari et al., "A kinetic study of biohydrogen production from glucose, molasses and cheese whey by suspended and attached cells of *Thermotoga neapolitana*," Bioresour. Technol., 2013, 147:553-61.
Hatch and Hardy, Microorganisms as producers of feedstock chemicals, A Revolution in Biotechnology, 1989, 28-41.

(Continued)

*Primary Examiner* — Christian L Fronda
(74) *Attorney, Agent, or Firm* — Fish & Richardson P.C.

(57) ABSTRACT

This disclosure describes methods that allow for the uncoupling of microbial growth from product formation, which allows for maximal use of raw material and optimal end-product formation.

6 Claims, 18 Drawing Sheets

Specification includes a Sequence Listing.

(56) References Cited

OTHER PUBLICATIONS

International Preliminary Report on Patentability in International Application No. PCT/US2016/028647, dated Nov. 2, 2017, 9 pages.
International Search Report and Written Opinion in International Application No. PCT/US2016/028647, dated Dec. 9, 2016, 23 pages.
Jessen & Orlygsson, "Production of ethanol from sugars and lignocellulosic biomass by Thermoanaerobacter J1 isolated from a hot spring in Iceland," J. Biomed. Biotechnol, 2012, 186982.
Karel et al., "The immobilization of whole cells: engineering principles," Chem. Eng. Sci, 1985, 40:1321-1354.
Keasling et al., "A toolkit for metabolic engineering of bacteria," BioHydrogen, 1998, 87-97.
Kind et al., "Metabolic engineering of cellular transport for overproduction of the platform chemical 1,5-diaminopentane in Corynebacterium glutamicum," Metab Eng, Sep. 2011, 13: 617-627.
Lacis and Lawford, "Ethanol production from xylose by Thermoanaerobacter ethanolicus in batch and continuous culture," Arch. Microbiol, May 1988, 150:48-55.
Lamed and Zeikus, "Ethanol Production by Thermophilic Bacteria: Relationship Between Fermentation Product Yields of and Catabolic Enzyme Activities in Clostridium thermocellum and hermoanaerobium brockii," Journal of Bacteriology, 1980, 144: 569-578.
Latif et al., "The Genome Organization of Thermotoga maritima Reflects Its Lifestyle," PLoS Genet, 2013, 9:e1003485.
Maezato et al., "Engineering thermoacidophilic archaea using linear DNA recombination," Methods in Molecular Biology, 2011, 765:435-45.
Michel-Savin et al., "Control of the selectivity of butyric acid production and improvement of fermentation performance with Clostridium tyrobutyricum," Applied Microbiology and Biotechnology, 1990, 32: 387-392.
Nelson et al., "Evidence for lateral gene transfer between Archaea and Bacteria from genome sequence of Thermotoga maritima," Nature, May 1999, 399: 323-329.
Nogales et al. "An in silico re-design of the metabolism in Thermotoga maritima for increased biohydrogen production." International Journal of Hydrogen Energy, 2012, 37: 12205-12218.

Pinto et al., "Rubisco mutants of Chlamydomonas reinhardtii enhance photosynthetic hydrogen production," Applied Microbiology and Biotechnology, 2013, 97: 5635-5643.
Pirt, "The maintenance energy of bacteria in growing cultures," Proc. R. Soc. Lond. B. Biol. Sci., Oct. 1965, 163(991):224-31.
Saveson and Lovett, "Tandem repeat recombination induced by replication fork defects in Escherichia coli requires a novel factor, RadC," Genetics, May 1999, 152:5-13.
Shaw et al., "Natural competence in Thermoanaerobacter and Thermoanaerobacterium species," Applied Environ. Microbiol, 2010, 76:4713-9.
Sigurbjornsdottir and Orlygsson, "Combined hydrogen and ethanol production from sugars and lignocellulosic biomass by Thermoanaerobacterium AK54, isolated from hot spring," Applied Energy, 2012, 97:785-91.
Taylor et al., "Thermophilic ethanologenesis: future prospects for second-generation bioethanol production," Trends in Biotechnology, 2009, 27: 398-405.
Thauer et al., "Energy conservation in chemotrophic anaerobic bacteria," Bacteriol Rev, 1977, 41(1):100-180.
Tunner et al., "Phenotypic characterization of two carbon starvation-inducible regulatory regions for recombinant protein production using growth attenuated Escherichia coli," Biotech. Bioeng. 1990, 40:271-279.
Wang et al., "Elimination of Rubisco alters the regulation of nitrogenase activity and increases hydrogen production in Rhodospirillum rubrum," International Journal of Hydrogen Energy, 2010, 35: 7377-7385.
Woodward et al., "Enzymatic production of biohydrogen," Nature, 2000, 405: 1014-1015.
Worthington et al., "Targeted disruption of the alpha-amylase gene in the hyperthermophilic archaeon Sulfolobus solfataricus," J. Bacteriol, 2003, 185:482-488.
Zhang et al., "High yield hydrogen production from starch and water by a synthetic enzymatic pathway," PLoS One, 2007, 2: e456.
Zhu and Yang, "Effect of pH on metabolic pathway shift in fermentation of xylose by Clostridium tyrobutyricum," Journal of Biotechnology, 2004 110: 143-157.

* cited by examiner

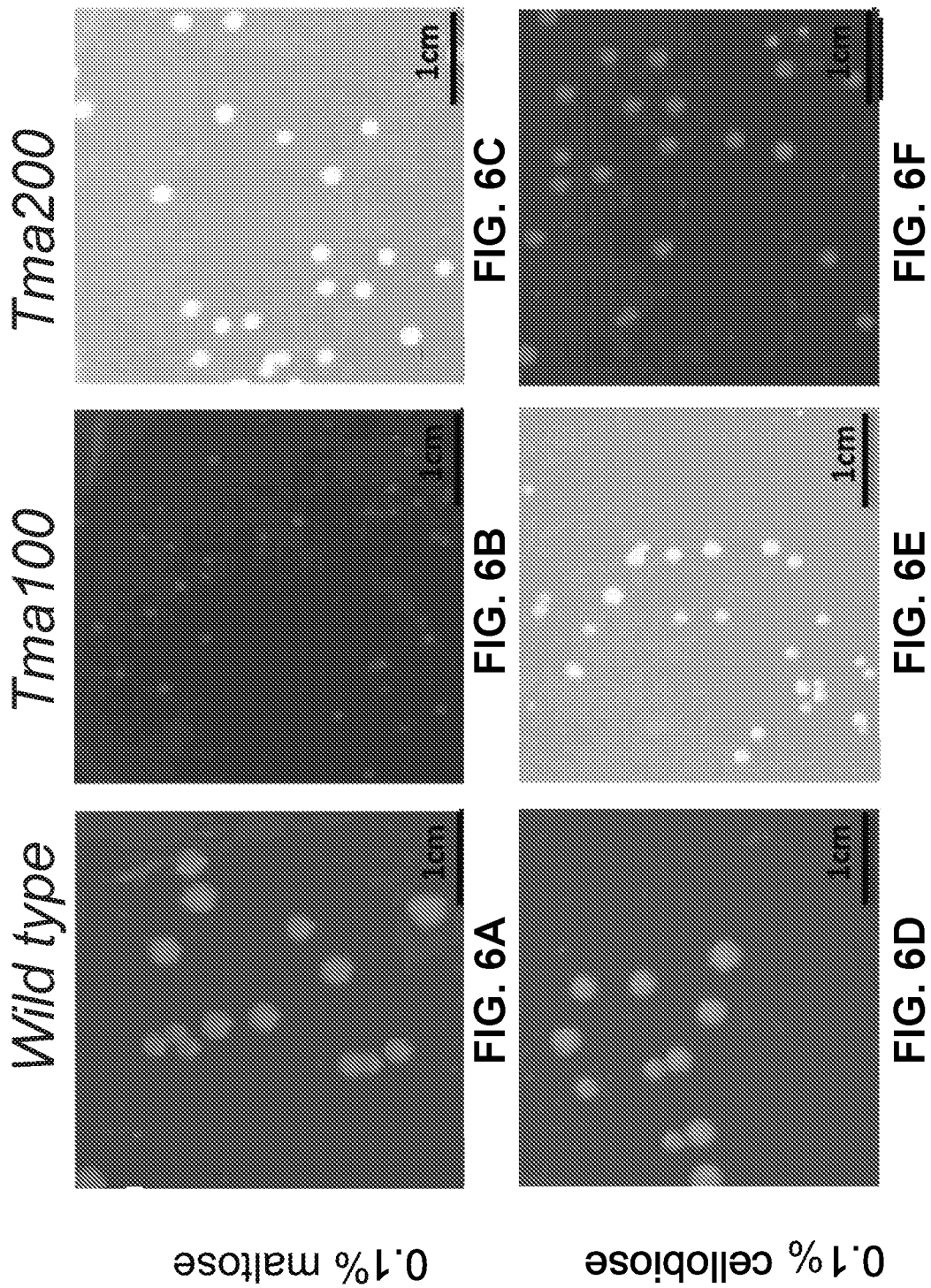

FIG. 7B

MUTANT MICROORGANISMS AND METHODS OF MAKING AND USING

CROSS-REFERENCE TO RELATED APPLICATION

This application is a National Stage Application under 35 U.S.C. § 371 and claims the benefit of International Application No. PCT/US2016/028647 filed Apr. 21, 2016, which claims priority under 35 U.S.C. § 119(e) to U.S. Application No. 62/150,345 filed Apr. 21, 2015. The disclosure of the foregoing applications are hereby incorporated by reference in their entirety.

FEDERALLY SPONSORED RESEARCH OR DEVELOPMENT

This invention was made with government support under DE-PS02-08ER08-12 and DE-FG02-08ER64687 awarded by the U.S. Department of Energy. The government has certain rights in the invention.

SEQUENCE LISTING

This application contains a Sequence Listing that has been submitted electronically as an ASCII text file named "Sequence_Listing.txt". The ASCII text file, created on Jul. 19, 2021, is 32 kilobytes in size. The material in the ASCII text file is hereby incorporated by reference in its entirety.

TECHNICAL FIELD

This disclosure generally relates to microorganisms.

BACKGROUND

The yield of biologically produced metabolites are constrained by the energy inherent to the starting substrates or by the toxicity of the resulting products. The methods described herein can be used to overcome these constraints and establish bio-renewable sources of energy or chemicals using microbial systems.

SUMMARY

In one aspect, a method of making a mutant microorganism that produces an increased amount of a biologically-produced metabolite relative to a microorganism lacking the mutation(s) is provided. Such a method typically includes: disrupting, transiently, a gene in a microorganism, thereby producing a transiently disrupted microorganism; passaging the transiently disrupted microorganism a plurality of times under selective pressure to produce a compensating microorganism; screening the compensating microorganism for an increase in one or more metabolites; and isolating the compensating microorganism having an increase in the desired metabolite. In some embodiments, the method further includes sequencing the genome of the compensating microorganism.

In some embodiments, the transient disruption is targeted to a gene in a pathway that, when disrupted, results in toxicity to the microorganism. In some embodiments, the transient disruption is chromosomal recombination. In some embodiments, the selective pressure is the toxicity resulting from the chromosomal disruption. In some embodiments, the selective pressure is selection with an antibiotic or other selectable marker. In some embodiments, the microorganism is a hyperthermophilic anaerobe and, in such embodiments, the cultivating takes place at or above 80° C.

In some embodiments, when the microorganism is a hyperthermophilic anaerobe and the biologically-produced metabolite is $H_2$, the gene targeted for transient disruption is lactate dehydrogenase. In some embodiments, when the microorganism is a photoautotrophic bacteria and the biologically-produced metabolite is $H_2$, the gene targeted for transient disruption is RUBISCO. In some embodiments, when the microorganism is selected from the group consisting of *Saccharomyces cerevisiae, Zymomonas mobilis*, and hyperthermophiles (Thermanaerobacter spp. and Caldicellulociruptor bescii) and the biologically-produced metabolite is ethanol, the gene targeted for transient disruption is selected from the group consisting of lactate dehydrogenase and acetate kinase. In some embodiments, when the microorganism is *Clostridium butyricum* and the biologically-produced metabolite is lactate, acetate or succinate, the gene targeted for transient disruption is selected from the group consisting of butyraldehyde dehydrogenase, lactate dehydrogenase, and acetaldehyde dehydrogenase/Acetyl CoA transferase. In some embodiments, when the microorganism is selected from the group consisting of *Caldicellulosiruptor bescii, Thermoanaerobacter ethanolicus, Thermoanaerobacterium saccharolyticum, Caldicellulosiruptor thermocellum* and the biologically-produced metabolite is ethanol, the gene targeted for transient disruption is selected from the group consisting of lactate dehydrogenase and acetate kinase and, optionally, hydrogenase. In some embodiments, when the microorganism is *Corynebacterium glutamicum* and the biologically-produced metabolite is an amino acid, the gene targeted for transient disruption is a corresponding amino acid transporter.

In another aspect, a *Thermotoga maritima* strain having at least one mutation is provided. Such a *T. maritima* mutant strain overproduces molecular hydrogen ($H_2$). In some embodiments, the mutation is in the ATP-binding component of a maltose ABC transporter. In some embodiments, the strain overproduces acetate. In some embodiments, the strain produces little to no lactate.

In some embodiments, the genotype of the strain comprises TM0460 (W229Stop), TM1276 (G148E), TM1276 (E345L), and TM1318 (L44L or 149I). In some embodiments, the genotype of the strain comprises TM0459 (A1045V), TM0460 (W229Stop), TM1276 (V233S) and a deletion at TM1323-TM1332. In some embodiments, the genotype of the strain comprises TM0459 (A1045V), TM0460 (W229Stop), TM1276 (V233F), and a deletion at TM1323-1332.

In still another aspect, a method of increasing the yield of molecular hydrogen ($H_2$) produced by *Thermotoga maritima* in culture is provided. Such a method typically includes: inactivating, transiently, the lactate dehydrogenase gene in the *T. maritima* using a selectable marker to produce an inactivated *T. maritima*; passaging the inactivated *T. maritima* a plurality of times under selective pressure to produce a compensating *T. maritima*, wherein the compensating *T. maritima* comprises a compensating mutation; screening the compensating *T. maritima* for an increase in $H_2$; and selecting/isolating the compensating *T. maritima* having an increase in $H_2$. In some embodiments, the method further includes sequencing the compensating *T. maritima*.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A

FIG. 4 is data showing the fermentation profile of wild type, Tma100 and Tma200. Strains were cultivated in a 3 L fermenter.

FIG. 6 are photographs showing the colony size variation in Tma strains. Wild-type, Tma100 and Tma200 grown on complex medium plates supplemented with 0.1% maltose (Panels A, B and C) or 0.1% cellobiose (Panels D, E and F), respectively. The Tma100 formed smaller colonies on CM plates with 0.1% maltose (Panel B) and bigger colonies on CM plates with 0.1% cellobiose (Panel E) comparative to Tma200 colonies on CM plates with 0.1% cellobiose (Panel F). Tma200 formed same size colonies on 0.1% maltose (Panel C) and 0.1% cellobiose (Panel F) as compared to the wild type control on CM plates (Panels A and D) containing different carbon sources. Scale bar is equal to 1 cm.

Part B

Figure 9:
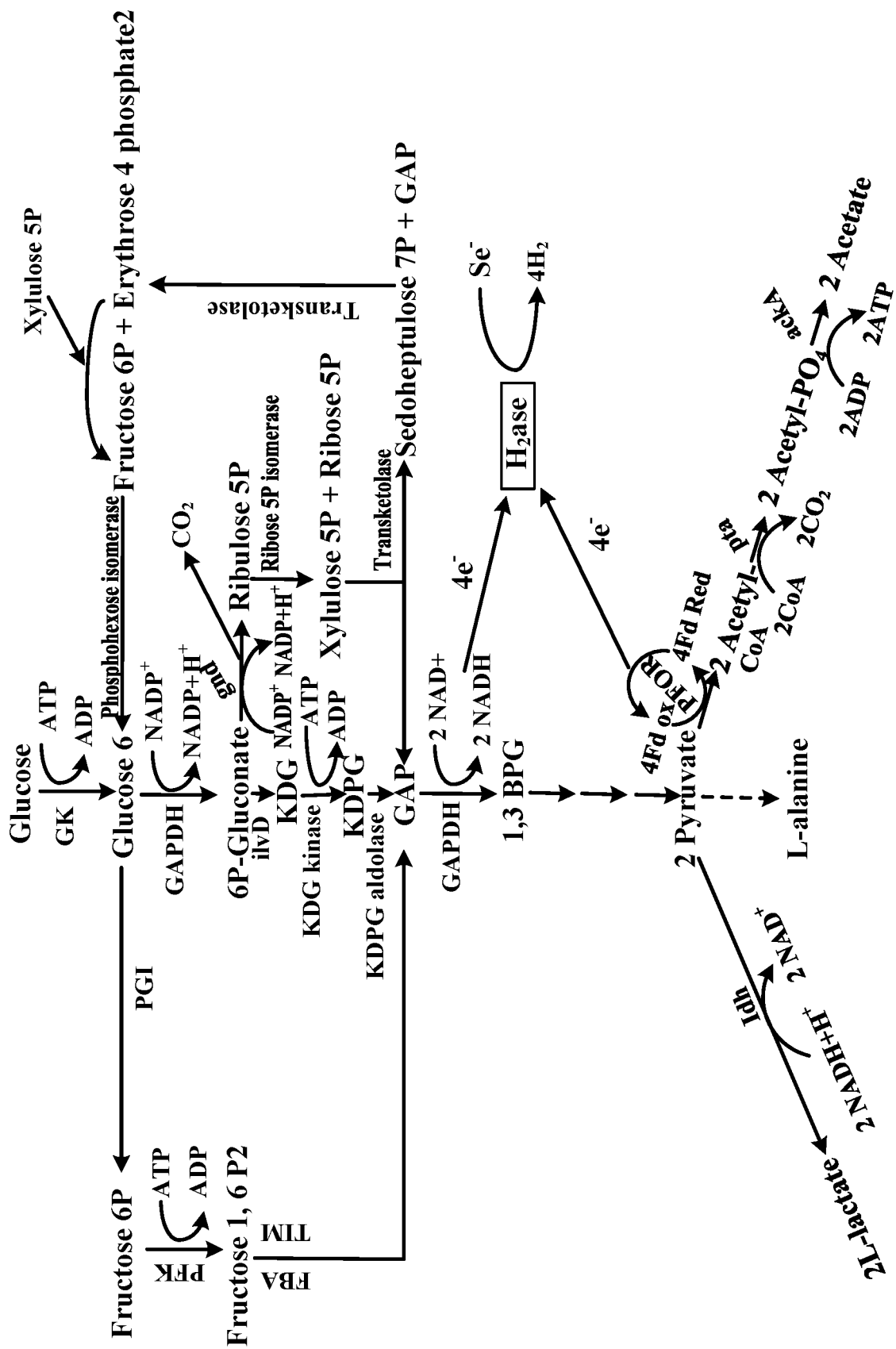

FIG. 9 shows the proposed central metabolic pathways in *T. maritima*. GK=Glucose kinase, PGI=Phosphoglucose isomerase, PFK=Phosphofructokinase, FBA=Fructose-1, 6bisphosphate aldolase, TIM=Triose-phosphate isomerase, G6PDH=Glucose-6-phosphate dehydrogenase, ilvD=Phosphogluconate dehydratase, gnd=6-phosphogluconate dehydrogenase, KDG=2-keto-3-deoxygluconate, KDPG=2-Keto-3-deoxy-6phosphogluconate, GAP=Glyceraldehyde-3-phosphate, 1,3 BPG=1,3-bisphosphoglycerate, GAPDH=Gly ceraldehy de-3phosphate dehydrogenase, $H_2$ase=Hydrogenase, ldh=lactate dehydrogenase, PFOR=Pyruvate Ferredoxin, Pta=Phosphate acetyltransferase, ackA=Acetate kinase.

Figure 10:
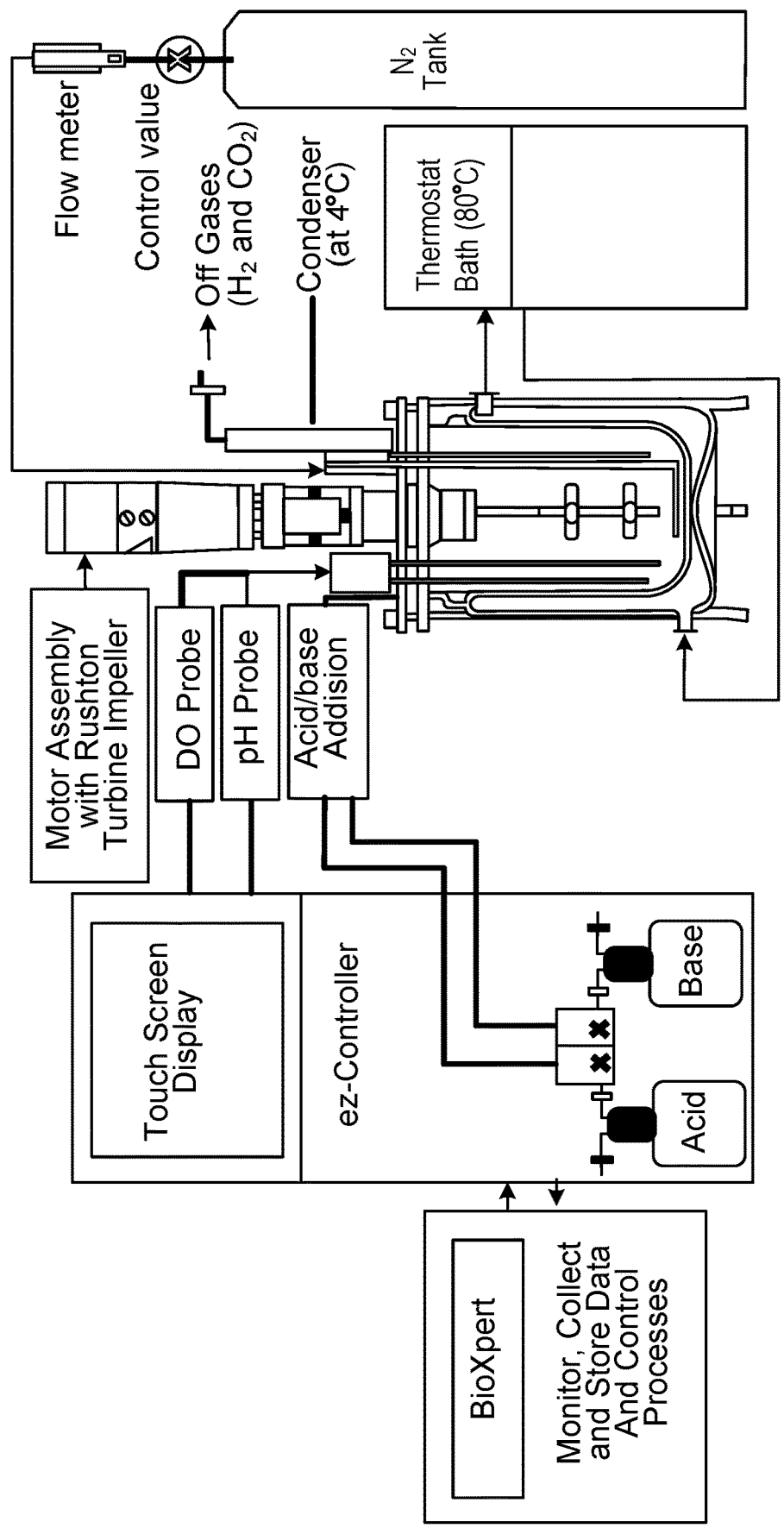

FIG. 10 is a schematic representation of a 3 L anaerobic fermenter set-up for wild type, Tma100 and Tma200, with associated control units and data acquisition system.

FIG. 11 shows the fitting of experimental values of growth, maltose consumption, H2 production and acetate production in wild type, Tma100 and Tma200. Experimental: wild type (●), Tma100 (▲) and Tma200 (■). Fitting wild type (—), Tma100 (----) and Tma200 ( . . . . ).

Figure 12:
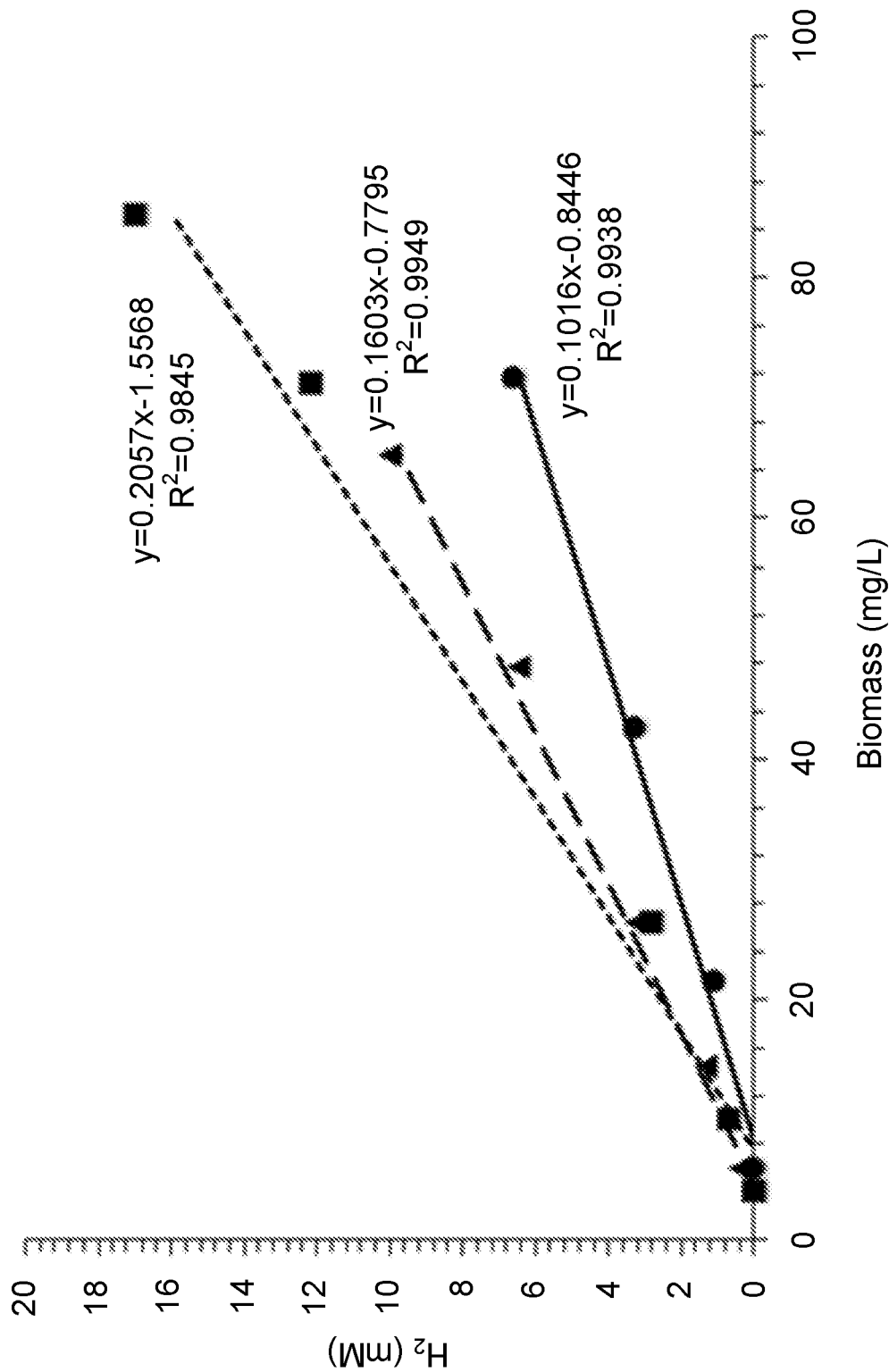

FIG. 12 shows the relationship between biomass and H2 production for wild type, Tma100 and Tma200. Slope represents the H2 production rate per mg cdw/L biomass.

Figure 5:
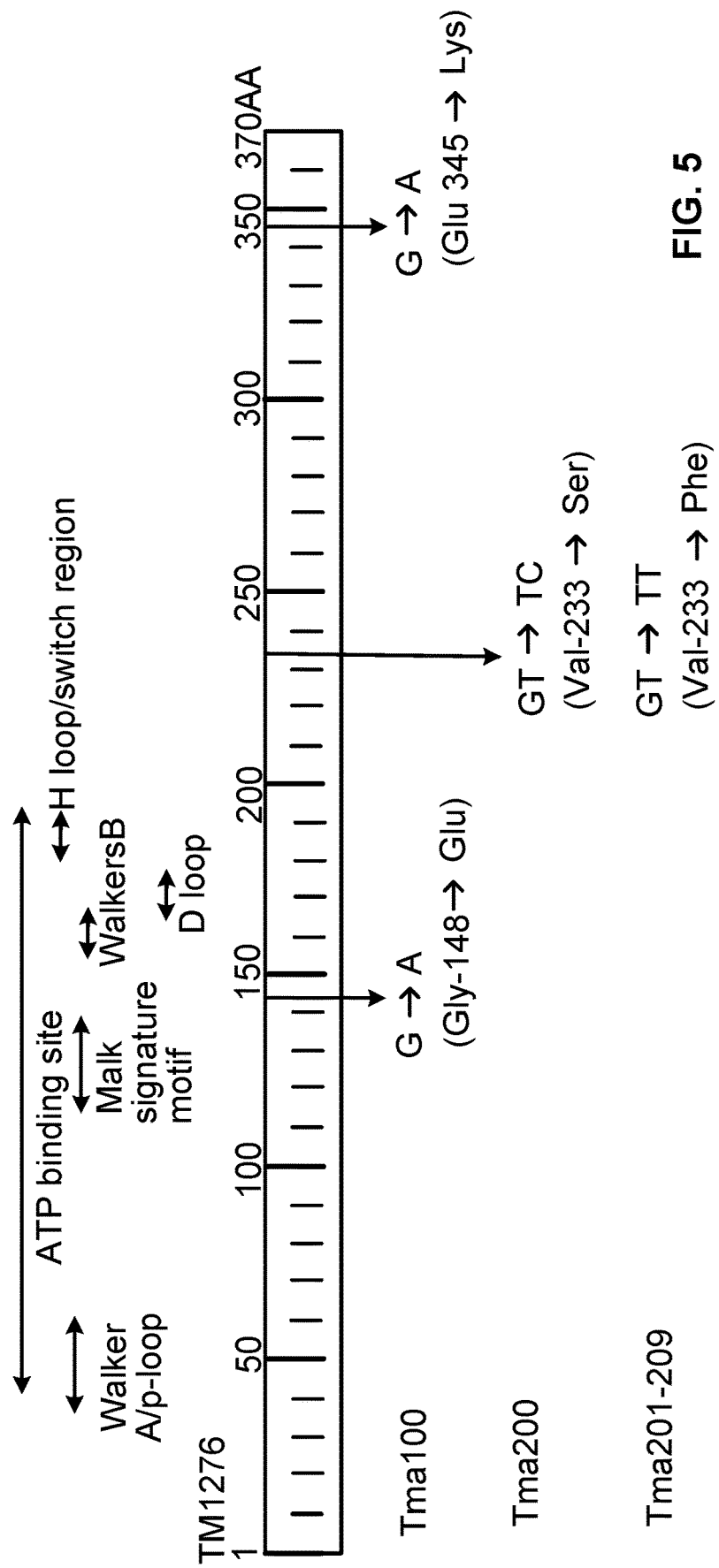
FIG. 5 is a schematic showing the domain structure and mutations of TM1276 (MalK). The diagram shows the features and predicted domain analysis of MalK of *T. maritima*. The location of substitution mutations in malK are indicated by vertical arrows for Tma100, Tma200 and Tma201-Tma209 along with their corresponding coordinates. Tma100 developed a mutation of G145E located near the signature motif but inside the ATP binding domain of MalK whereas other mutation of E345L remained located at 3' end. Tma200 and Tma201-209 developed a unique mutation at $233^{rd}$ amino acid which is away from the ATP binding domain.

FIG. 5 shows the continuous flow simulation for biomass, maltose utilization, $H_2$ production and acetate production in wild type (—), Tma100 (----) and Tma200 ( . . . ).

Figure 13:
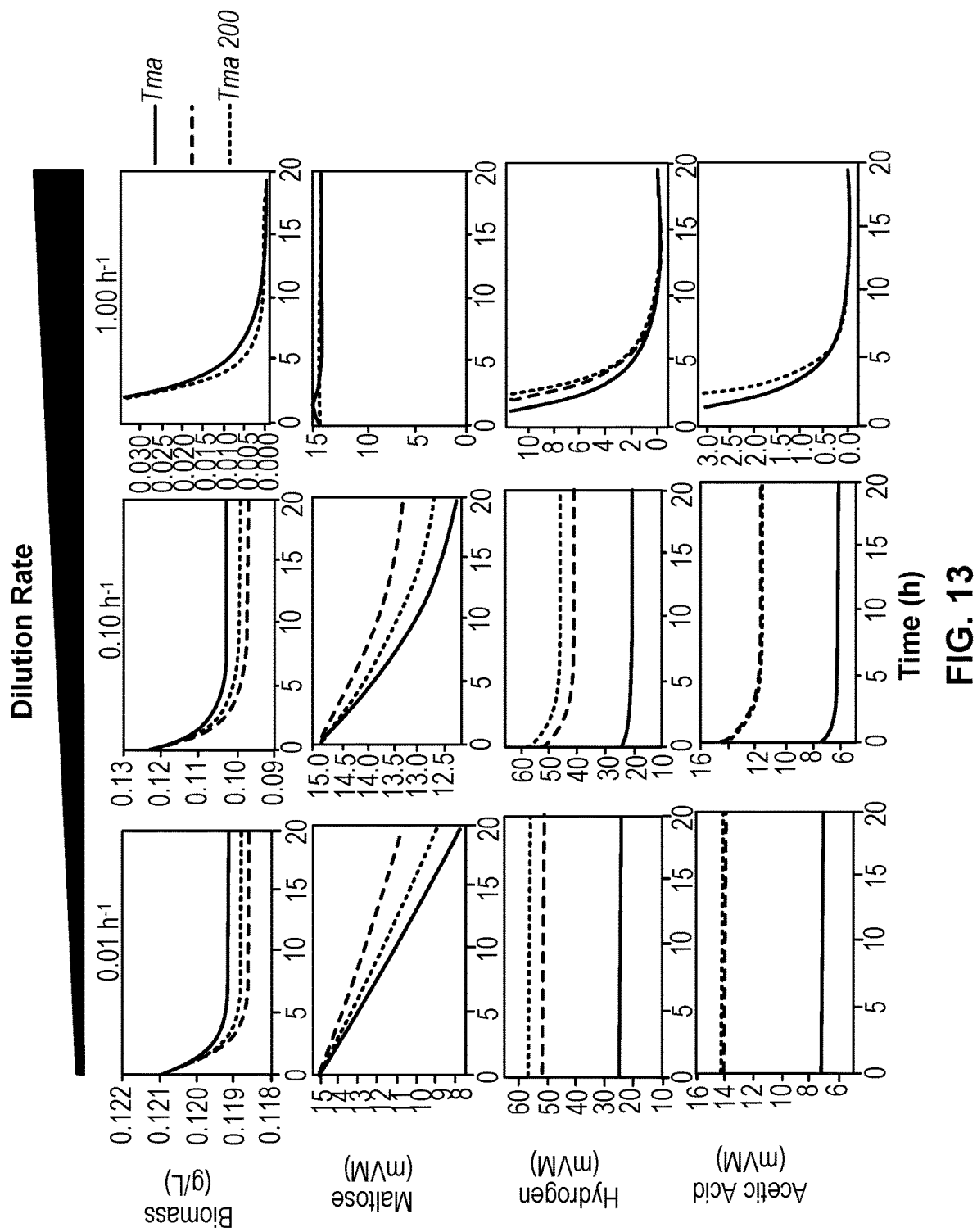

FIG. 13 are graphs showing the comparative simulation results for all the cell lines at three different dilution rates.

Figure 14B:
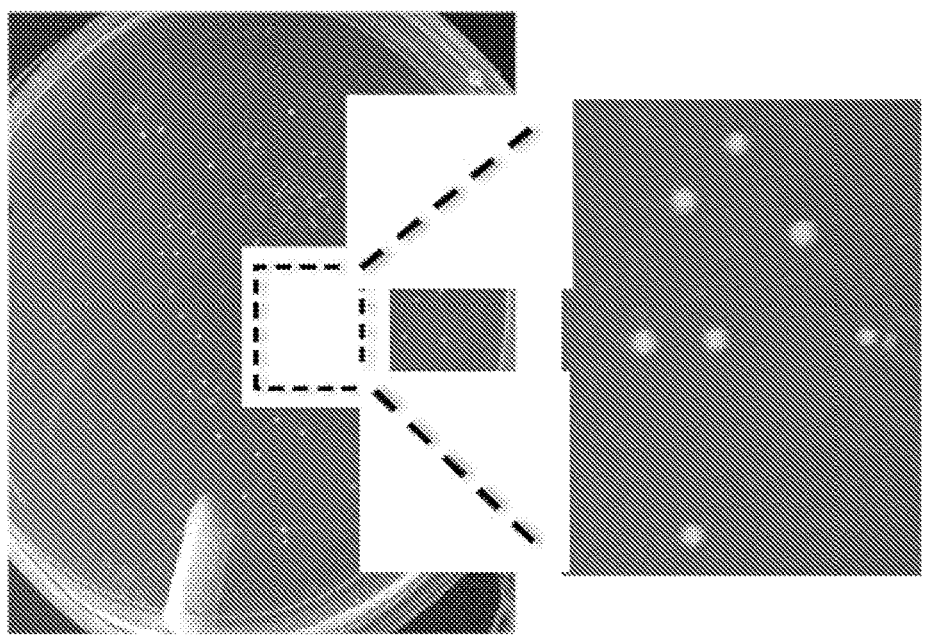
Figure 14A:
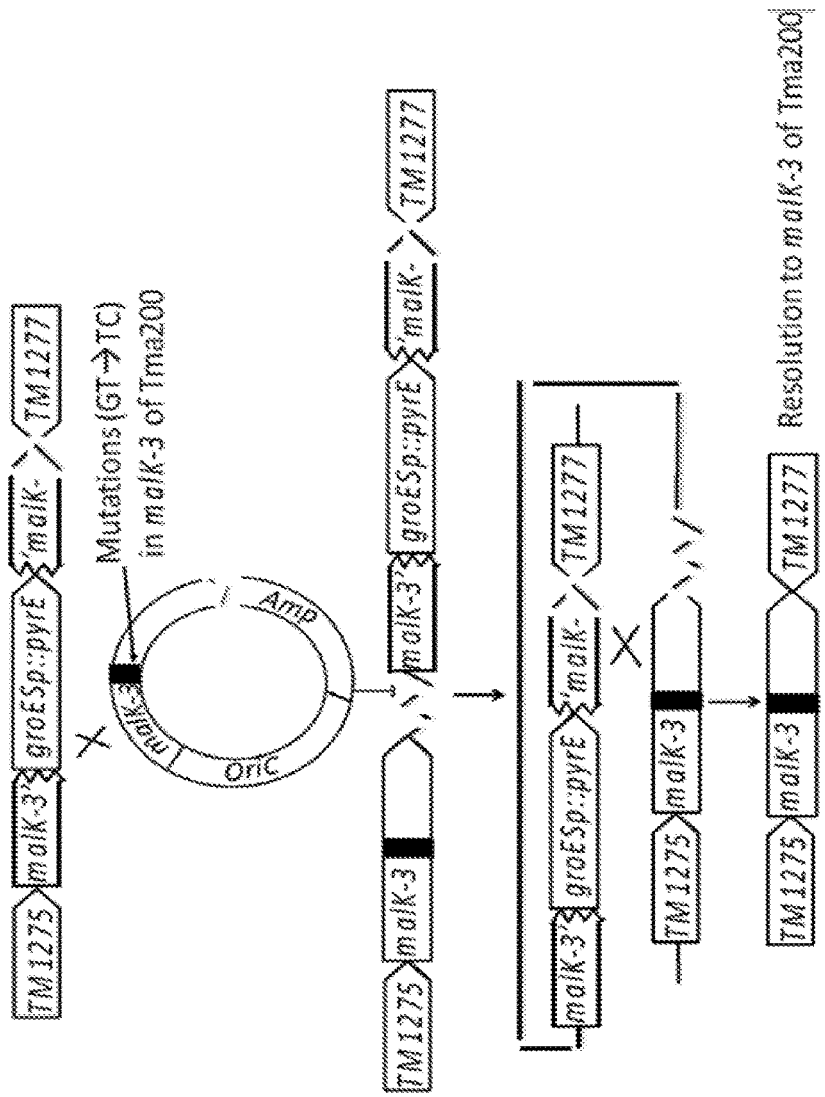
Figures 14C, 14D, 14E:
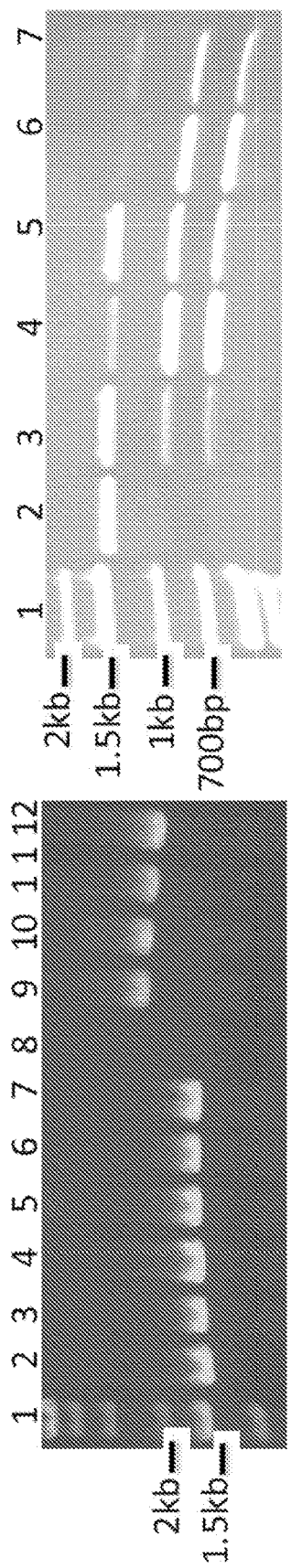

FIG. 14A is a schematic showing crossover at the disrupted malK-3 allele of the malK-3 mutant and resolution into a strain possessing malK-3 allele of Tma200. FIG. 14B shows the colony phenotype of the strain repaired with malK-3 of Tma200. FIG. 14C is a gel of the nucleic acid products from PCR amplification of the malK-3 locus of the bigger colonies (lanes 2-7) and small colonies (lanes 8-12). FIG. 14D is a gel showing a restriction digestion of the PCR amplicon of bigger colonies (lane 3-7) and wild type (lane-2) with AciI. FIG. 14E is a sequence alignment of the malK-3 locus of the two isolates representing mutations in the malK-3 similar to the malK-3 of Tma200 strain.

Figure 15:
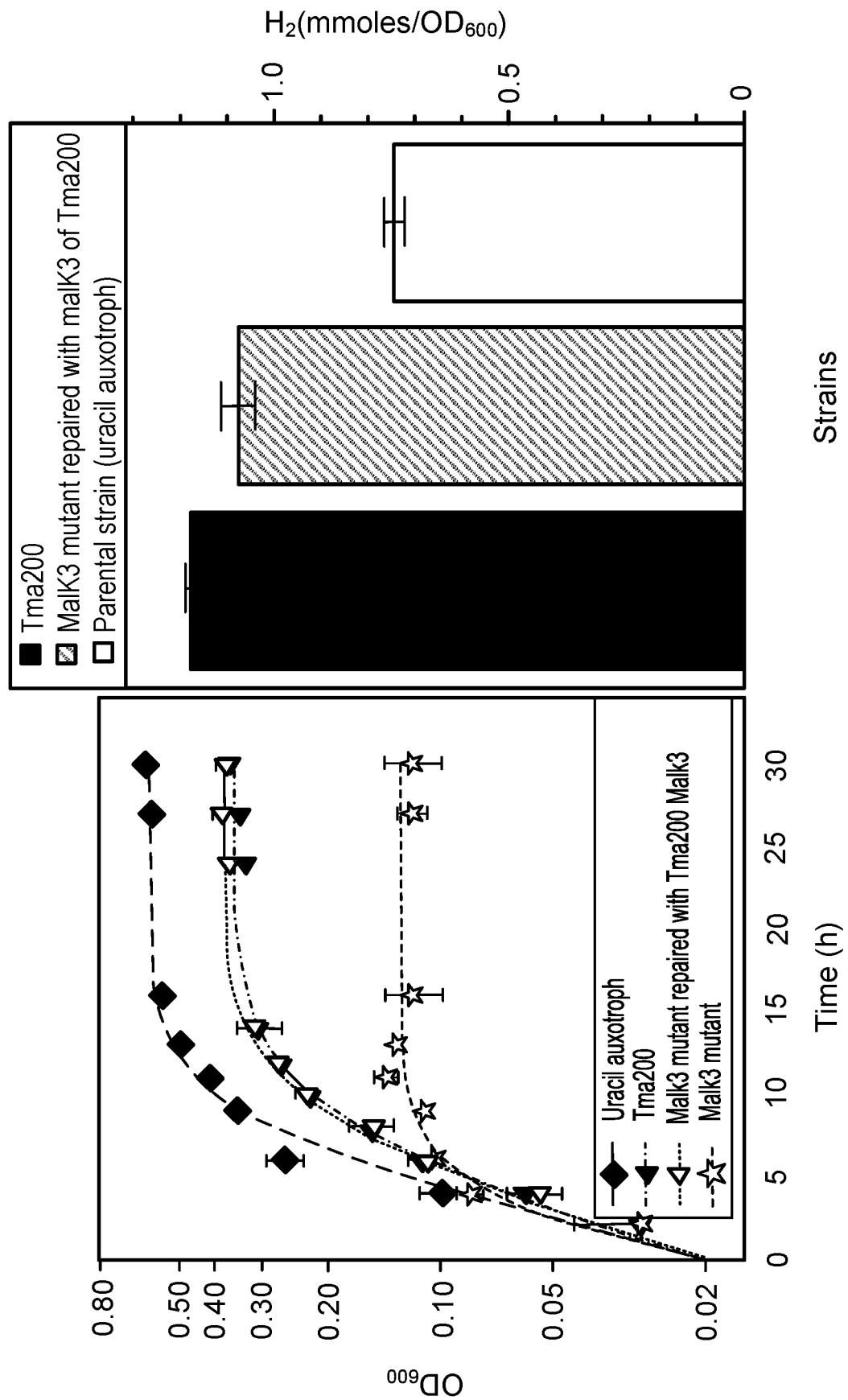

FIG. 15 are graphs showing the growth curve (left) and hydrogen production (right) from a reconstructed strain containing the malK-3 of Tma200, original Tma200 and the parental strain.

DETAILED DESCRIPTION

The differences between theoretical and physiological yields of an in vivo metabolite arise from the energetic cost of forming new cell mass. For this reason, maximizing the amount of raw material used for end-product synthesis while minimizing by-product formation (e.g., cell mass) requires uncoupling microbial growth from product formation. Slow growth, rather than no growth, may be required to support the needs of energy-coupled reactions and to maintain oxidation-reduction balance. Maintaining oxidation-reduction balance in a microorganism also can be referred to as redox homeostasis, which is a concept that is central to the methods described herein. Redox homeostasis is the critical requirement of all living cells to maintain a balance between oxidized and reduced cellular components. Metabolism comprises a large and very significant segment of a cell's oxidized and reduced components. Their oxidation/reduction state (often referred to as the "redox state") must be maintained within a narrow range in order for life to be maintained.

Theoretically, 12 mole of $H_2$ can be formed per mole of glucose, and this has been verified in vitro when preformed converting enzymes were supplied along with ATP and NADH (Woodward et al., 2000, Nature, 405:1014-5; Zhang et al., 2007, PLoS One, 2:e456). However, the resulting Gibbs free energy is −9.5 Kcal under standard conditions and, therefore, only 31% of the energy needed to form ATP (from ADP). Consequently, in whole cells, Thauer proposed a physiologic limit of 33%, or 4 mole $H_2$ per mole of glucose, to enable sufficient energy formation to support cell growth (Thauer et al., 1977, Bacteriol. Rev., 41(1):100-80). Significantly, using the transient gene inactivation methods described herein, cell lines were produced that exceed the physiologic (or Thauer) limit for hydrogen production. Although not wishing to be bound by any particular theory, it is believed that the phenomenon described herein results from a reduction in the rate of cell growth and an increase in electrons that became available for hydrogen formation.

The methods described herein can be used to make a mutant microorganism that produces an increased amount of a biologically-produced metabolite relative to a microorganism lacking the mutation(s). These methods can be used to increase the maintenance energy coefficient of a microorganism and, surprisingly, allow for limitations related to the requirements of maintenance energy in a microorganism to be overcome. Maintenance energy represents all cellular functions except those associated with biomass formation. Therefore, maintenance energy is inclusive of metabolite formation.

The method described herein can be used to increase the amount of any number of biologically-produced metabolites (e.g., metabolites that are integral to the maintenance of redox homeostasis). For example, biologically-produced metabolites as used herein can refer to $H_2$, ethanol, lactate, acetate, succinate, glutathione, ferrodoxin, pyridine nucleotides, one or more amino acids, one or more antibiotics, nutraceuticals, one or more small molecules, or compounds derived from those metabolites or intermediates thereof including, without limitation, secondary metabolites.

The methods described herein typically begin with transient disruption of a gene to produce a transiently disrupted microorganism. The gene that is transiently disrupted in a microorganism is dependent upon the particular metabolite, and the metabolic pathways involved in the production of that metabolite. The gene that is transiently disrupted in a microorganism typically is a gene related to the production of a metabolite that maintain redox homeostasis in a microorganism. One or more metabolites can maintain redox homeostasis through their excretion, thereby removing an excess of reductant (e.g., as a reduced metabolite in an anaerobic organism) or by removing an excess of oxidant (e.g., as an oxidized metabolite in an aerobic organism). Perturbing redox homeostasis creates an unsustainable metabolic state, which can either be lethal to the microorganism or can result in one or more mutations (referred to herein as compensatory mutations) so as to allow the microorganism to overcome, or resolve, the redox imbalance.

As described herein, the gene that can be transiently disrupted in the methods described herein can be, without limitation, lactate dehydrogenase (e.g., for an increase in the amount of $H_2$, ethanol, lactate, acetate, and/or succinate), butyraldehyde dehydrogenase (e.g., for an increase in the amount of lactate, acetate, and/or succinate), acetaldehyde dehydrogenase (e.g., for an increase in the amount of lactate, acetate, and/or succinate), acetyl CoA transferase (e.g., for an increase in the amount of lactate, acetate, and/or succinate), RUBISCO (e.g., for an increase in the amount of $H_2$), acetate kinase (e.g., for an increase in the amount of ethanol), hydrogenase (e.g., for an increase in the amount of ethanol), or one or more amino acid transporters (e.g., for an increase in the amount of one or more amino acids). In some instances, the gene that is transiently disrupted is an essential gene or encodes a product that is essential or required in, for example, a metabolic pathway.

As used herein, "transient disruption" refers to a gene disruption that is not permanent and that can revert back to the non-mutant state (e.g., wild type). Disruption typically results from homologous recombination resulting from a single crossover event (see, for example, FIG. 2), which is genetically unstable. Once the microorganism has compensated for the metabolic and/or physiologic stress caused by the disrupted gene (e.g., by introducing compensatory mutations), the unstable locus undergoes recombination again to revert back to its original state (i.e., the state prior to disruption, e.g., wild type). Methods for achieving transient disruption are known in the art. See, for example, Blum et al. (1989, J. Bacteriol., 171:538 546) and Worthington et al. (2003, J. Bacteriol., 185:482-488).

The transiently-disrupted microorganism then is passaged a plurality of times under selective pressure for a phenotype that imposes a metabolic constraint. In some instances, the gene targeted for transient disruption is a gene in a pathway that, when disrupted, results in toxicity to the microorganism. In certain instances, such toxicity can function as the selective pressure. In certain instances, an antibiotic or another type of selective pressure can be applied to the microorganism (e.g., in culture), for example, to maintain selection on the transient disruption. This type of additional selection can prolong the time necessary for the microorganism to compensate for the transient disruption, thereby increasing the likelihood that one or more of the compensatory mutations will increase the yield of one or more metabolites.

Although not wishing to be bound by any particular theory, passaging the transiently disrupted microorganism under selective pressure results in the introduction of one or more mutations that allows the microorganism to compensate appropriately. A desirable mutation, as described herein, is one that leads to production of the metabolite at levels that exceed those produced by a corresponding microorganism grown under the same or essentially the same conditions but lacking the mutation(s). An increase in the production of a metabolite at levels that exceed those produced by a microorganism that does not contain the mutation(s) typically arises from a change in metabolism that shifts energy away from biomass formation (or cellular reproduction) and toward metabolite formation (or maintenance energy).

Once a microorganism is identified (i.e., a microorganism that produces an increased amount of the desirable metabolite), such a microorganism can be isolated if so desired. Methods of isolating microorganisms are known in the art. Optionally, the method can further include sequencing the genome of the compensating microorganism to determine the mutational basis for the increased metabolite yield. There are a number of methods available for sequencing genomes including, without limitation, any number of next-generation sequencing methods (e.g., Illumina (Solexa) sequencing; massively parallel signature sequencing (MPSS); pyrosequencing; Ion Torrent semiconductor sequencing; single molecule sequencing; SOLiD sequencing; single molecule real time (SMRT) sequencing).

The methods described herein are not limited to any particular microorganism provided, of course, that the particular microorganism produces at least some amount of the desired metabolite. Representative microorganisms are hyperthermophilic anaerobes, but microorganisms include, for example, photoautotrophic bacteria, *Saccharomyces cerevisiae, Zymomonas mobilis*, hyperthermophiles (e.g., Thermanaerobacter spp. and *Caldicellulosiruptor bescii*), *Clostridium butyricum, Caldicellulosiruptor bescii, Thermoanaerobacter ethanolicus, Thermoanaerobacterium saccharolyticum, Caldicellulosiruptor thermocellum*, and/or *Corynebacterium glutamicum*. Cultivation conditions are well known or can be readily determined for any such microorganism.

As used herein, an "increase" in the amount of a metabolite refers to an increase (e.g., a statistically significant increase) in the metabolite by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to a corresponding microorganism lacking the mutation(s) (i.e., when grown under corresponding conditions). Similarly, an "increase" in the maintenance energy coefficient refers to an increase (e.g., a statistically significant increase) in the maintenance energy coefficient of at least 1.1-fold up to 2-fold or more relative to a microorganism lacking the mutation(s). As used herein, statistical significance refers to a p-value of less than 0.05, e.g., a p-value of less than 0.025 or a p-value of less than 0.01, using an appropriate measure of statistical significance, e.g., a one-tailed two sample t-test.

The method described herein was applied to increase the yield of molecular hydrogen ($H_2$) produced by *Thermotoga maritima* in culture. First, the lactate dehydrogenase gene in T. maritime was transiently inactivated using a selectable marker. Second, the inactivated *T. maritima* was passaged a plurality of times under selective pressure to produce a compensating mutation, and screened to identify a mutant *T. maritima* that exhibits an increase in $H_2$. Next, the mutant *T. maritima* exhibiting an increase in $H_2$ was purified, and the genome of the mutant *T. maritima* was sequenced to identify the particular mutation(s) present.

A similar strategy can be employed to increase the yield of molecular hydrogen ($H_2$) in a microorganism (e.g., a photoautotrophic bacteria) by transiently disrupting the RUBISCO gene. In this case, the selective pressure applied to the transiently disrupted microorganism redirects metabolism towards hydrogen production by enhancing the availability of both reductant and energy. Under photoautotrophic conditions, transient inactivation of RUBISCO would be lethal because it would block carbon assimilation while simultaneously shifting consumption of reductant and energy away from carbon reduction. The transient accumulation of reductant then selects for compensatory mutations such as mutation of acetyl-CoA synthetase, which normally compensates for an increase in the ATP pool generated via the TCA cycle. Increased availability of ATP combined with increased availability of reductant promote increased levels of hydrogen because hydrogen synthesis depends on both energy and reductant. The resulting mutant bacteria that produces an increased amount of $H_2$ can be purified and, if desired, the genome sequenced to identify the mutation(s).

Likewise, a similar strategy can be employed to increase the yield of ethanol in a microorganism (e.g., *Saccharomyces cerevisiae, Zymomonas mobilis*, and hyperthermophiles (Thermanaerobacter spp. and Caldicellulociruptor bescii) by transiently disrupting the lactate dehydrogenase gene and/or the acetate kinase gene. In this case, the selective pressure applied to the transiently disrupted microorganism can be prolonged by maintaining selection using, for example, one or more antibiotics while cultivating the microorganism under fermentative conditions that naturally promote ethanol synthesis. The resulting mutant bacteria that produces an increased amount of ethanol can be purified and, if desired, the genome sequenced to identify the mutation(s) present.

A similar strategy can be employed to increase the yield of ethanol in a microorganism (e.g., *Caldicellulosiruptor bescii, Thermoanaerobacter* ethanolicus, *Thermoanaerobacterium saccharolyticum, Caldicellulosiruptor thermocellum*) by transiently disrupting the lactate dehydrogenase gene and/or the acetate kinase gene and, optionally, the hydrogenase gene. In this case, the selective pressure applied to the transiently disrupted microorganism can be prolonged by maintaining selection using, for example, one or more antibiotics while cultivating the microorganism under fermentative conditions that naturally promote ethanol synthesis. The resulting mutant bacteria that produces an increased amount of ethanol can be purified and, if desired, the genome sequenced to identify the mutation(s).

Similarly, such a strategy can be employed to increase the yield of lactate, acetate, and/or succinate in a microorganism (e.g., *Clostridium butyricum*) by transiently disrupting the butyraldehyde dehydrogenase gene, the lactate dehydrogenase gene, and/or the acetaldehyde dehydrogenase/Acetyl CoA transferase genes. In this case, the selective pressure applied to the transiently disrupted microorganism can be prolonged by maintaining selection using, for example, one or more antibiotics while cultivating the microorganism under fermentative conditions that naturally promote synthesis of organic acids. The resulting mutant bacteria that produces an increased amount of lactate, acetate, and/or succinate can be purified and, if desired, the genome sequenced to identify the mutation(s).

The strategy described herein also can be employed to increase the yield of one or more amino acids in a microorganism (e.g., *Corynebacterium glutamicum*) by transiently disrupting a corresponding amino acid transporter. In this case, the selective pressure applied to the transiently disrupted microorganism can be prolonged by maintaining selection using, for example, one or more antibiotics while cultivating the microorganism under fermentative conditions that naturally promote amino acid synthesis. The resulting mutant bacteria that produces an increased amount of one or more amino acids can be purified and, if desired, the genome sequenced to identify the mutation(s).

Also described is a *Thermotoga maritima* strain produced by the method above. The *T. maritima* strain includes at least one mutation and overproduces molecular hydrogen ($H_2$). The strain also overproduces acetate and produces little to no lactate. As described herein, it was determined that the compensating mutation is in the ATP-binding component of a maltose ABC transporter. A representative strain made by the method described herein has the genotype: TM0460 (W229Stop), TM1276 (G148E), TM1276 (E345L), and TM1318 (L44L or I49I). Another representative strain made by the method described herein has the genotype: TM0459 (A1045V), TM0460 (W229Stop), TM1276 (V233S) and a deletion at TM1323-TM1332. Still another representative strain made by the method described herein has the genotype: TM0459 (A1045V), TM0460 (W229Stop), TM1276 (V233F), and a deletion at TM1323-1332.

Also as described herein, kinetic modeling can be performed to explore the interrelationship between various excreted metabolites. Such modeling can allow the prediction of outcomes in continuous fermentation systems, which would facilitate commercial production of one or more metabolites (e.g., $H_2$).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1—Bacterial Strains and Cultivation

*Thermotoga maritima* MSB8 was purchased from the American Type Culture Collection (ATCC) and cultured routinely in a complex medium (CM). CM contained 0.26 M NaCl, 0.05% (w/v) Tryptone, 0.01% (w/v) Yeast extract, 14 mM $Na_2SO_4$, 9.8 mM $MgCl_2$-$6H_2O$, 3.0 mM $NaHCO_3$, 0.17 mM KBr, 0.12 mM KI, 0.32 mM $H_3BO_3$, 9 μM $Na_2WO_4$, and 8.4 μM $NiCl_2$ and was adjusted to pH 7.0 before autoclaving using $KH_2PO_4$. Autoclaved liquid CM was aliquoted into sterile Hungate tubes or serum bottles and amended by addition of sterile $Na_2S$ (42 μM), $KH_2PO_4$ (3.4 μM), and sugar (15 mM). *T. maritima* strains (Table 1) were cultivated in batch culture in biological replicates using Hungate tubes or serum bottles containing 10 mL or 50 ml CM respectively and supplemented with 0.5% (15 mM) maltose unless otherwise indicated. Tubes were sealed with butyl rubber stoppers (Bellco Biotechnology), crimped with metal collars and the head-space was exchanged with $N_2$. Growth was monitored spectrophotometrically by the culture absorbance at a wavelength of 600 nm. Sterile 1 cc syringes attached to 20½ G needles were used for inoculation at initial cell densities of 0.03 $OD_{600}$. All tubes were incubated anaerobically at 80° C. overnight unless specified before chemical analysis. For volumetric $H_2$ productivity measurements, strains were cultivated in 3 L double-jacketed glass bioreactors (Applicon, MA) with a 1.5-L working volume with continuous stirring at 200 rpm using dual axial impellers. Bioreactors were equipped with sensors monitoring temperature, pH and dissolved oxygen while an anaerobic environment was maintained by continuous supply of $N_2$ at 15 ml/minute. The pH was maintained at pH 7 by addition of acid (1 M $H_2SO_4$)/base (1 M NaOH) via a peristaltic pump. To minimize water loss, water vapor in the outlet headspace gas was condensed using a chilled water supply and returned to the vessel.

TABLE 1

Bacterial Strains and Plasmids

| Strain/Plasmid | Description/genotype | Reference(s) or source |
|---|---|---|
| Tma | *Thermotoga maritima* MSB8 (Wild-type) | ATCC |
| Tma100 | *T. maritima*; TM0460 (W229Stop), TM1276 (G148E and E345L) and TM1318 (L44L and I49I synonymous codon change) | This work |
| Tma200 | *T. maritima*; TM0459 (A1045V), TM0460 (W229Stop), TM1276 (V233S) and ΔTM1323-TM1332 | This work |
| Tma200 to Tma1100 | *T. maritima*; TM0459 (A1045V), TM0460 (W229Stop), TM1276 (V233F) and ΔTM1323TM1332 | This work |
| pBL1292 | pUC57; *T. maritima* ldhΔ3':groESp::HTK | This work |

(SEQ ID NO: 15)
TM1276:
MRMAQVVLENVTKVYENKVVAVKNANLVVEDKEFVVLLGPSGCGKITTLRM

IAGLEEITDGKIYIDGKVVNDVEPKDRDIAMVFQNYALYPHMTVYENMAFG

LKLRKYPKDEIDRRVREAAKILGIENLLDRKPRQLSGGQRQRVAVGRAIVR

NPKVFLFDEPLSNLDAKLRVQMRSELKKLHHRLQATIIYVTHDQVEAMTMA

DKIVVMKDGEIQQIGTPHEIYNSPANVFVAGFIGSPPMNFVNARVVRGEGG

LWIQASGFKVKVPKEFEDKLANYIDKEIIFGIRPEDIYDKLFALAPSPENT

ITGVVDVVEPLGSETILHVKVGDDLIVASVNPRTQAKEEQKIDLVLDMTRM

HAFDKETEKAII (SEQ ID NO: 16)
TM0460:
MKKLFVLFLAVLSVLVLAEVKNPDTIIDATIGEPDTLDPHFAYDTASGEVI

YNVYENLIAYKGESLTEFEPRLAERWEILDDGKTYKFYIRKGVKFHEGGDL

TPEDVEYSFERGLIFDPTAGPMWMLWEALFGVDSLETFVEEKIGKPYSELF

DENGEPLPEYRDALIKIYTDYIDPAIEVEGDAVVFHLVRPFAPFMYILAQS

ASWSAVLDKEWCIEIGCWDGRADTWWKYHDIRKEDSPLYARMNGTGPFKFV

EWDRAQQKVILERNDNYWREPAKIKRVIIWGIDEWSTRRAMFLQGDADICA

VPTQYLEQVEGKPGVIVVKGLPELAVTSLHFAWNVPEDSKYIGSGKLDGNG

IPPDFFSDENVRKAFIYAFDYDTFINEVLKGLGRKIPTDLPEGLLGFNEEL

LNDPDAPHFDIVKATEYFKKAWNGEVWKKGFKITLLYNTGNEVRRQAAEML

KAYIEMINPKFKVEVRGVQWPTYLDATKRGEVPAFIIGWLADYPDHNFIF

TYYHSAGVYSGRQGENFRKFVSTPHPDLGGRSLDELIEEAIAKTDPAERQA

LYEEIQRFAMKHALGMPLYQPLGVRVQRSWVKGWYHNPMRPGDDYYVLWKA

EE

-continued

TM1323:
(SEQ ID NO: 17)
MIIFLILVLLSTIIFADKVKTDNETHSWKSEITEQVQVAPKSAATCEVTFK

GSTAGNQSF

TM1332:
(SEQ ID NO: 18)
MKMKGIESLKEIFKYGAFSLPVANYLLCEGNIPGDCKRILDVLKLAWKGNF

KEAIRRADKAVENSRSETAKYFLLANKLVFLKYTGKVDMNLYRYLKRNLPK

MSKSIRDTVIVTLINFEASGVKPLRKMRVWKNNYRKSTLSFLYLSLARREA

DSGDLSEAVHGYIQAYKLSREIPHPTCMVSSLNDLAWDIKEKHPKLAYDLS

KGAVFWLGYYREEPGNLFGALDTLFVVEKDMDSPSIHSTAHIIVSLPVPED

YLSLLKKAKKFVLDYTGSTYPNTSQLRRYVEKVAWKGKTLSSKGISDILKG

KTKMIRADTIRKLLTSGVDTGAPFPVWNEWIKMEIERKYRESSEKLKELPF

HQRQILFLTTYMALLDREFLSRKEKLKKAYTLLEDIESFADFMAKDHRTME

FVVSMVKAHPFVEGRKEAVKRALARMKRKRLERFVLRYIEMKESDRKLLDR

FLRNYGRYDGVRFGIRLKGPEVVREFAKKYSLKVQPLFAAFWCEEDGRVRR

RLERILKYMFLN

A solid medium was prepared by combining 0.6% (w/v) gelrite (Research Product Corporation, IL) solubilized by boiling with previously sterilized complex medium components followed by addition of reductant (Na$_2$S), base (KH$_2$PO$_4$) and carbon sources as indicated. For preparation of drug plates, kanamycin was added at the amounts indicated to the medium prior to pouring. Inoculated plates were incubated at 80° C. for 2-3 days in jars (Almore) under anaerobic conditions using gaspacks (EZ BD). Long term preservation of cultures was as described previously for other hyperthermophiles.

Example 2—Strain Construction

The chromosomal ldh gene was inactivated by targeted recombination via a single crossover event. A 3' terminally truncated segment of ldh (Nelson et al., 1999, Nature, 399:323-9; genomic coordinates 1848586-1849070) was cloned into pUC19 (using P1 and P2 primers, Table 4) and flanked with the kanamycin nucleotidyltransferase gene (htk) under the control of the *T. maritima* groESLp heat shock promoter (using P3 and P4 primers). The first codon of HTK was fused to the 3' end of groESp at nt position 532232 (Nelson et al., 1999, supra). Ligation, transformation and selection of *E. coli* (DH5α) positive transformants was performed as previously described. The resulting ldh gene disruption construct (pBL1292, Table 1) was transformed into wild-type *T. maritima* spheroplasts prepared as described with the following modifications. Proteinase K (10 mg/mL) was used in combination with lysozyme (300 μg/mL) mL and the efficiency of spheroplast formation was monitored by light microscopy. Spheroplasts ($7.5 \times 10^7$ cells) were electroporated (1.8 kV, 200Ω and 25 μF) with a maximum of 1 μg of plasmid DNA using a Genpulser (BioRad) in chilled 1 mm cuvettes. Electroporated spheroplasts were inoculated into complex liquid medium and incubated anaerobically at 80° C. for 18 hours. For initial screening, 100 μL of recovered cells were subjected to drug selection by addition of 375 μg/mL kanamycin. Genomic DNA was recovered from the enriched culture and genotyped to verify recombination at ldh. Transformation efficiency was determined on plates containing 500 μg/mL kanamycin and normalized to values on plates without added drug. Colonies were purified on 0.5% (w/v) maltose plates containing 500 μg/mL kanamycin by spot dilution. Genomic DNA from strain Tma100 was prepared as described for other hyperthermophiles and genotyped by PCR and DNA sequencing to confirm the presence of groESp::HTK, vector sequences and the presence of 5' and 3' flanking ldh flanking sequences.

TABLE 4

Primers

| Primer | Sequence | Restriction sites | SEQ ID NO: |
|---|---|---|---|
| P1 (5'ldhF) | 5' ATGAAAATAGGTATCGTAGGACTCG 3' | EcoR-I | 1 |
| P2 (3'ldhR) | 5' CTTGGAGAAAAGCCGCAGT 3' | EcoR-V | 2 |
| P3 (groESpF) | 5' GCTTCAAGCGCCTTTTTATTT 3' | BamHI | 3 |
| P4 (HTKR) | 5' TCAAAATGGTATTCTCTTGCTAACG 3' | BamHI | 4 |
| P5 (TM1866R) | 5' TCGGGCAAGATCCCCCATGGA 3' | N/A | 5 |
| P6 (lacZ212R) | 5' ATATGCGGTGTGAAATACCGCA 3' | N/A | 6 |
| P7 (TM1868F) | 5' ATAGTGCCCCTTCTCATATC 3' | N/A | 7 |
| P8 (TM1866R1) | 5' GGCTAAACTAATTGAAAGTGACAGA 3' | N/A | 8 |
| P9 (HTKR1) | 5' TCGTATGAGAACTCAACACCTTCAGT 3' | N/A | 9 |
| P10 (BlaR1) | 5' GGGCGACACGGAAATGTT 3' | N/A | 10 |
| P11 (BlaF) | 5' ATAATACCGCGCCACATAGC 3' | N/A | 11 |
| P12 (Bla1R) | 5' CCCTTTTTTGCGGCATTT 3' | N/A | 12 |

Example 3—Cell Line Passage and Phenotypic Analysis

Passage of Tma100 on CM maltose plates was used to isolate more robust derivatives without concurrent selection for kanamycin resistance. Fifty colonies of Tma100 were patched on CM maltose (0.1% w/v) plates and incubated at 80° C. anaerobically. Ten isolates were then grown in CM tubes supplemented with maltose (0.5% w/v) and then screened by PCR for the groESp::HTK transgene. Colony phenotypes of selected strains were examined on plates with either maltose or cellobiose both at 0.1% (w/v) after anaerobic incubation at 80° C. for 48 hours.

Example 4—Analytical Methods

Analysis of head space gas composition was performed by withdrawing 500 µL volumes using a gas tight syringe (Hamilton) and injected into a gas chromatograph (GC 400 Series, GOWMAC, PA) fitted with a Thermal Conductivity Detector. A Molecular Sieve column (GOWMAC), operated at 70° C. with a continuous flow of $N_2$ carrier gas, was used to separate $H_2$. Calibration curves were obtained by injecting various volumes of the pure hydrogen and the amount of $H_2$ in the head space was estimated by comparison to these values. The molar yield of $H_2$ was calculated using the ideal gas law equation (PV=nRT) at standard temperature and pressure. Since growth varied among different cell lines in small batch cultures, $H_2$ values were normalized to $10^8$ cells/mL. Similarly, in bioreactor studies, the quantity of $H_2$ produced during exponential growth (5 hr duration) by Tma100 and Tma200 was normalized to the biomass produced by the wild type strain (Tma) under analogous growth conditions. Rates of $H_2$ production per hr in bioreactor studies was calculated for each growth phase and was normalized to mass as 1 g cell dry weight (cdw) for each strain. For biomass measurements, different amounts of washed cell pellets were dried and used to derive the conversion factor between optical density ($OD_{600nm}$ of 1.0) and dry weight of 0.2 milligrams. Organic acids and maltose concentrations were determined in culture supernatants by HPLC with comparison to standards. Prior to injection, samples were clarified at 10,000×g for 10 min and then filtered (AcroDisc, 0.45 µM). Samples (1 µL) were analyzed using an Agilent 1200 HPLC system and an automated sampler equipped with a Refractive Index Detector and a Hi-Plex H column (ChromTech) operated at 65° C. Isocratic separations used 4 mM sulfuric acid at a rate of 0.4 mL per minute. The regression equation was used to calculate aqueous metabolite concentrations. Yield coefficients were expressed as the ratio of moles of metabolites produced to the moles of maltose consumed.

Example 5—Transport Assays

Maltose transport assays were carried out as described for other anaerobes with the following modifications. Cells were cultivated in 50 mL CM supplemented with 0.5% (w/v) maltose and harvested at early mid log phase (optical density at 600 nm 0.25-0.35) followed by washing using CM twice. Washed cells were maintained under anaerobic conditions prior to transporter assays. Cell suspensions of 1.68 OD of cells in 1.5 mL were placed in anaerobic Hungate tubes for 30-40 min at 75° C. and allowed to equilibrate. Assays were initiated by addition of 20 µL of [$^{14}$C]maltose (American Radiolabeled Chemicals, St. Louis, Mo.) with a specific activity of 600 mCi/mmol at the indicated concentrations. To determine transport rates at higher substrate concentrations, unlabeled maltose ranging from 250 nM to 1000 nM was mixed with [$^{14}$C]-maltose (keeping the initial concentration of [$^{14}$C]-maltose same). [$^{14}$C]maltose uptake reactions were terminated at the times indicated by filtering 200 µL volumes of cells through a 0.45 µM polycarbonate (Whatman Nuclepore Track-Etch Membrane) with a fabricated and disposable polypropylene filtration apparatus. Cells retained on the filters were washed with 3 mL of CM. Backgrounds were determined using a no-cell sample processed in an otherwise identical fashion. Dried filters were placed in vials prefilled with 5 mL scintillant (EcoLite) and radioactivity determined using a scintillation spectrometer (Beckman LSC 6500). For the [$^{14}$C]-maltose uptake calculations, all uptake values were subtracted from the control reaction that was terminated immediately after the addition of [$^{14}$C]-maltose as described. [$^{14}$C]maltose uptake rates in all isolates were determined from the slope of the linear regression of total [$^{14}$C]-maltose transported as a function of time. No sampling was done between 0 and 15 sec as maltose uptake was faster immediately after this time. $K_m$ and $V_{max}$ values were determined by nonlinear regression fitting to the Michaelis-Menten equation. All rates were verified using biological replicates. The concentration of [$^{14}$C]-maltose stocks was measured experimentally rather than using a theoretical/nominal concentration.

Example 6—Genome Re-Sequencing

Genome re-sequencing was performed by DOE-JGI under a Community Sequencing Program (CSP) JGI project ID1011924. DNA was sequenced using a Hiseq Illumina instrument. IGV (ver. 2.3) was used to compare the genome of the three isolates with the latest genome sequence available at NCBI (NC_023151.1) (*T. maritima* MSB8 genomovar DSM 3109). Megablast was used to identify large genomic rearrangements. To evaluate domain-associated mutations, primarily substitutions, domain structure analysis was conducted using known protein structures available in the protein databank (PDB). Homology structural modeling used PHYRE. All mutations in Tma100 and Tma200 were verified by PCR and DNA re-sequencing and deletion endpoints were determined by sequencing overlapping amplicons spanning the deleted region.

Figure 1:
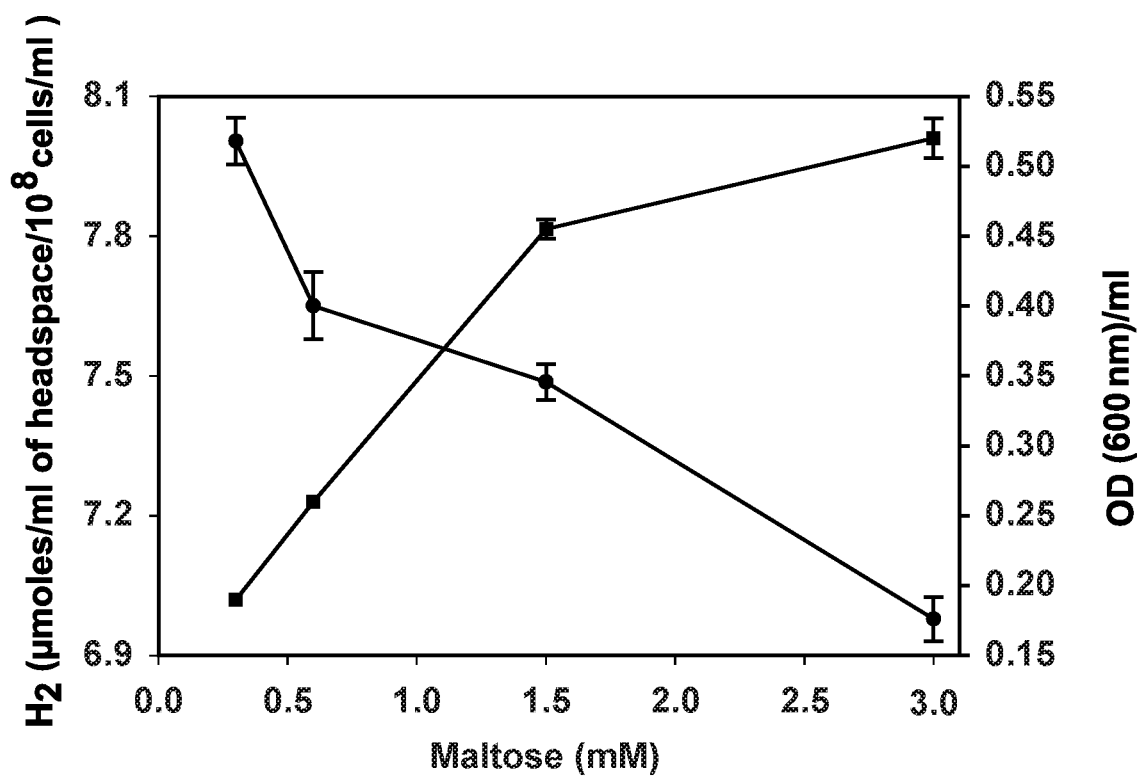
FIG. 1 is a graph showing the relationship between maltose concentration and $H_2$ production. $H_2$ production (●) and growth (■) of wild type (*T. maritima*) grown in various amounts of maltose in batch culture. Accumulated $H_2$ from each sugar concentration was normalized to $10^8$ cells/mL. The error bar represents the standard deviations from biological replicates.

Example 7—Isolation of $H_2$ Overproducing Cell Lines by Transient Gene Inactivation The growth inhibitory effect of $H_2$ has been reported for *T. maritima* as well as for other $H_2$ producing organisms. To assess the magnitude of this effect using small-batch culture-based methods appropriate for genetic manipulation, *T. maritima* was grown with various amounts of added maltose and the relationship between cell and $H_2$ yields was determined. Cell yields saturated rapidly with increasing maltose concentration (FIG. 1). $H_2$ production was normalized to cell mass to compare $H_2$ production at different concentrations of maltose. The apparent inverse relationship between $H_2$ levels and maltose concentration verified $H_2$ toxicity under these conditions. If this toxicity was sufficient to inhibit growth, it could be used to enrich for mutants that overcame this effect. Since an increase in $H_2$ partial pressure shifts the metabolism of *T. maritima* towards lactate synthesis and not ethanol, transient inactivation of ldh could exacerbate $H_2$ toxicity creating the necessary selective pressure to recover such mutants.

Example 8—*T. maritima* is Transformable Using Replicating Plasmids

Figure 2A:
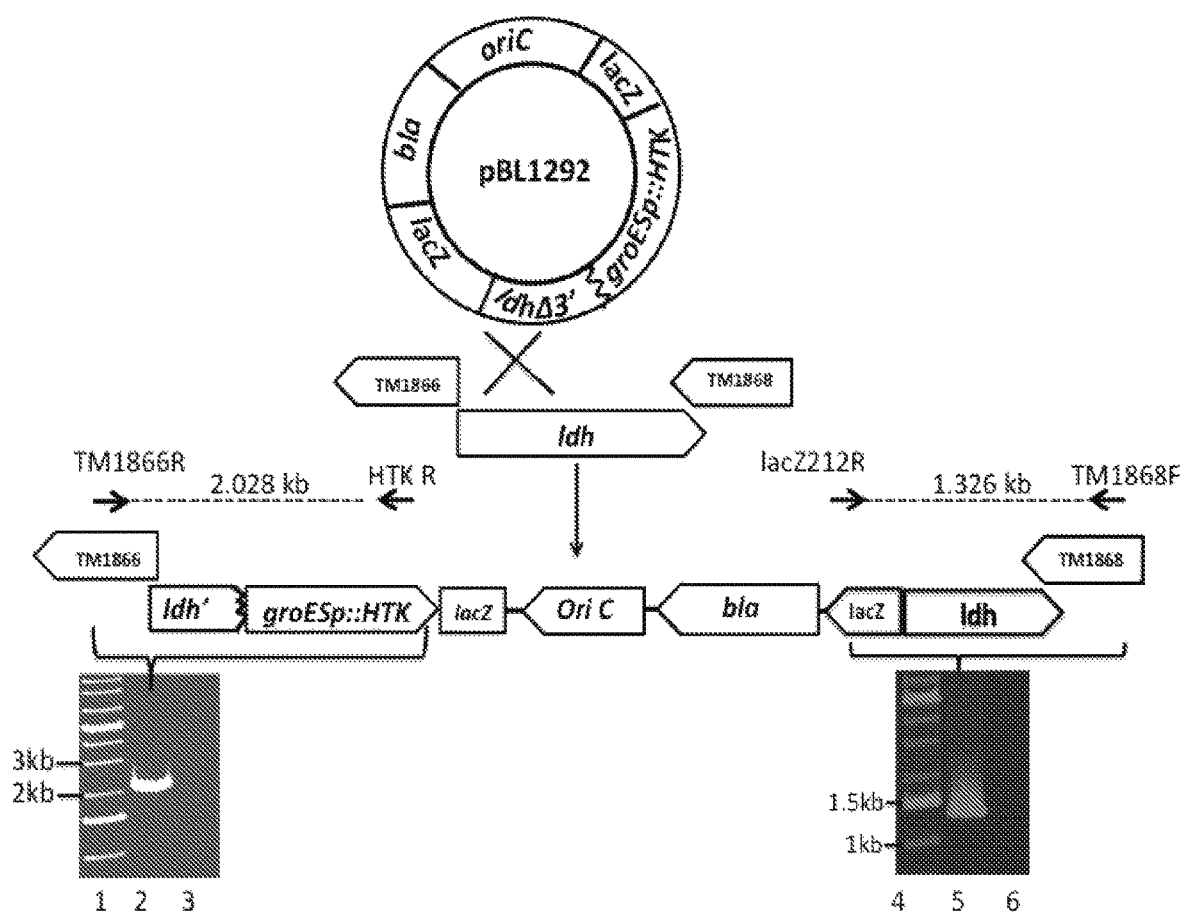
FIG. 2 demonstrates the targeted disruption of lactate dehydrogenase (ldh) via homologous recombination in *T. maritima*. Schematic of ldh disruption by single crossover and PCR amplification of predicted amplicons (FIG. 2A is liquid enrichment and FIG. 2B is Tma100). Lanes 1, 4, 7, 11, 16 and 19 represent molecular marker, Lanes 2, 3, 8, 9, 10 represent unique 5' fusion joint at ldh locus in liquid enrichment, wild type, Kan$^R$ mutant, Tma100 and wild type, respectively. Lanes 5, 6, 20, 21 and 22 represent and 3' fusion joint at ldh locus in liquid enrichment, wild type, Kan$^R$ mutant, wild type and Tma100, respectively. Lanes 12, 13, 14 and 15 represent selectable marker in pBL1292, wild type, Kan$^R$ mutant and Tma100, respectively. Lanes 17 and 18 represents bla gene in pBL1292 and Tma100.

Chromosomal recombination was therefore pursued as demonstrated previously for other hyperthermophiles. Cells were transformed with a 3' terminally truncated copy of ldh fused to a thermostable kanamycin resistance gene (HTK) driven by the *T. maritima* groESL promoter (groESLp). Electroporated cells were enriched for antibiotic resistant recombinants in liquid culture using selected concentrations of added drug depending on the selection process. Total genomic DNA was then screened for the presence of novel chromosomal fusions arising from targeted recombination at ldh. The predicted unique 5' amplicon (2046 bp) was evident following PCR amplification using a primer complementary to sequences upstream of ldh (P5) and the 3' end of HTK (P4) (FIG. 2A). Similarly, the predicted unique 3' PCR amplicon (1320 bp) was also detected using a lacZ primer (P6) and TM1868 F (P7). Both amplicons were detected using genomic DNA from enrichments using 375 µg/mL and 500 µg/mL of added kanamycin and their composition was verified by DNA sequencing. These results confirmed that directed chromosome recombination was successful and prompted efforts to recover recombinant clonal cell lines.

Figure 2B:
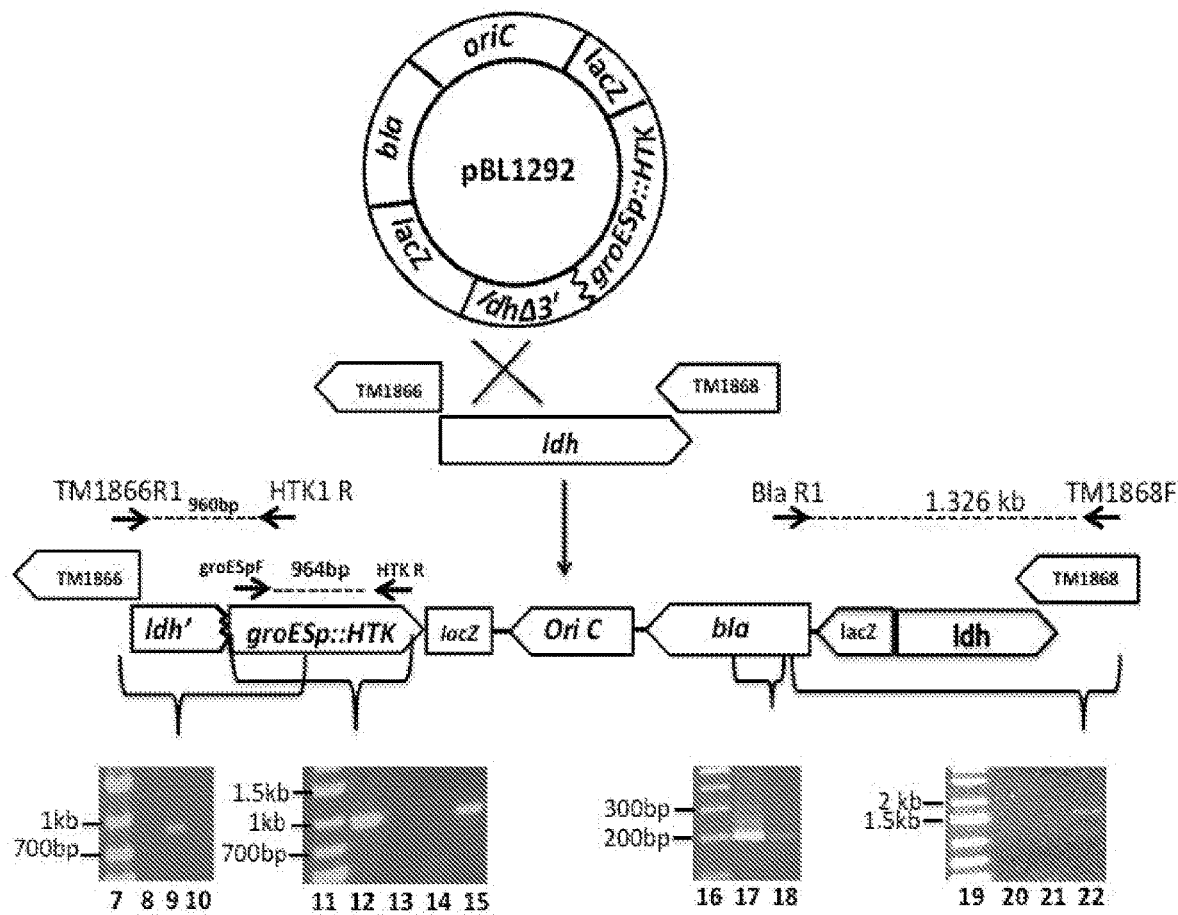
Figure 7A:
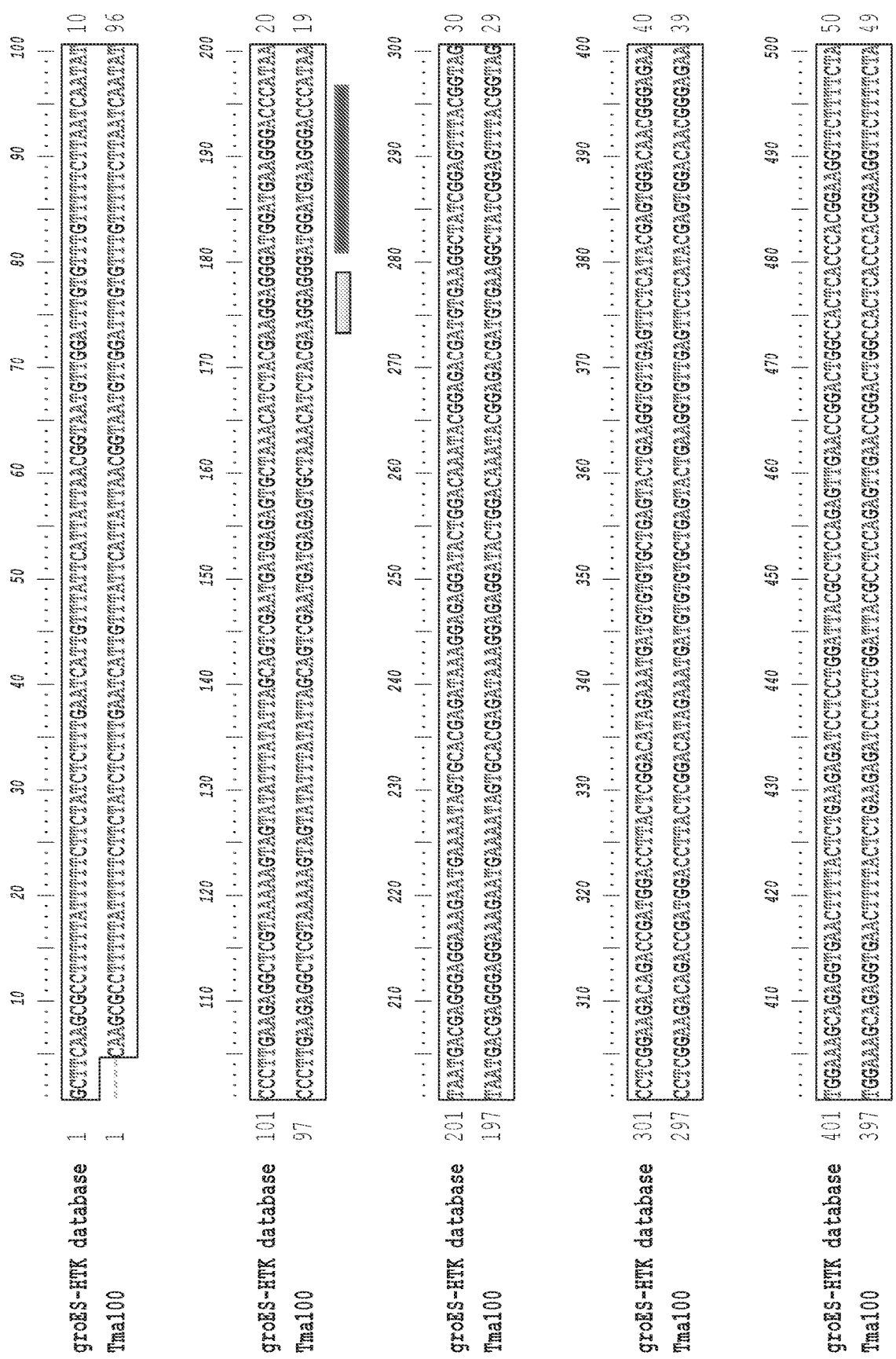
FIG. 7 is the sequence of the selectable marker (groESp:: HTK) from the database (SEQ ID NO:13) and in Tma100 (SEQ ID NO:14). The light box indicates the Shine-Dalgarno sequence and the dark box indicates the first codon of the kanamycin nucleotidyltransferase (HTK) gene.
Figure 7B:
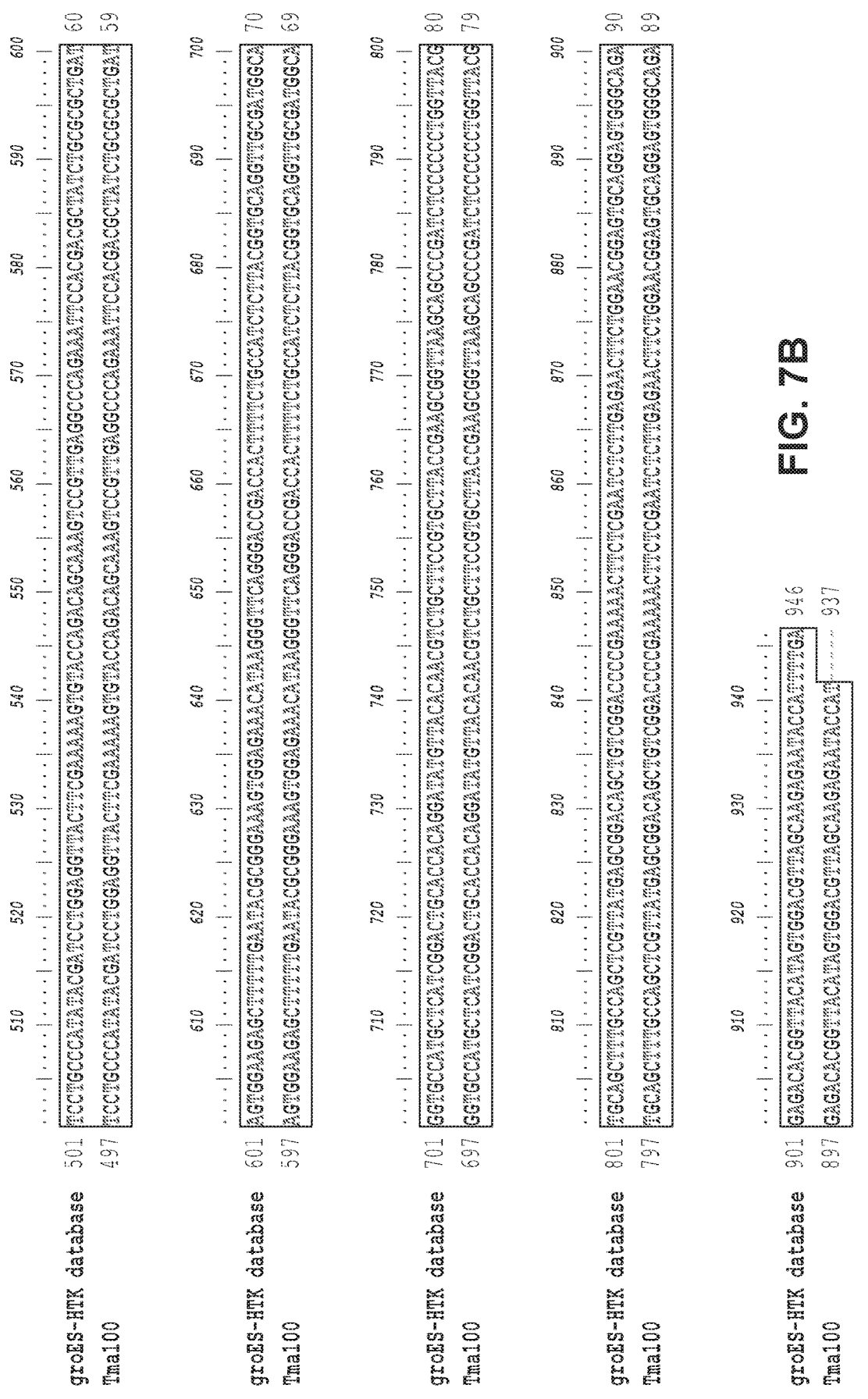

Direct plating of cells transformed in an identical manner yielded a 34-fold higher plating efficiency relative to untransformed cells though the overall efficiency was low (44 recombinants/µg DNA). Following purification to clonality with selection, PCR screening indicated the presence of the groESp::HTK transgene in 3 of 5 isolates. One isolate named Tma100 was then pursued for additional analysis (FIG. 2B). All predicted amplicons were evident using the indicated primers including; the genetic marker (groESp:: HTK, 946 bp) (P3, P4), a 5' unique fusion joint between the upstream gene and within the genetic marker (TM1866:: ldh::groESp::HTK, 960 bp) (P8, P9), a unique fusion joint between the 3' end of ldh and the non-replicating plasmid vector (bla::ldh:TM1868, 1729 bp) (P10, P7), and the vector encoded genetic marker (bla, 200 bp) (P11, P12). In addition, recombination at the groESL locus was excluded by the apparent absence of a PCR amplicon encoding ldh fused to this region. The identity of the genetic marker (groESp:: HTK) and 5' and 3' unique fusion joints in Tma100 mutant was confirmed by sequencing (FIG. 7). Together these data verified targeted integration at the chromosomal ldh locus. Subsequent passage of 50 isolates derived from Tma100 without drug selection followed by retesting of drug sensitivity indicated that all isolates retained kanamycin resistance. Ten of these isolates (Tma200 to Tma209) were then analyzed by PCR and all had lost the disrupted copy of ldh. DNA sequencing indicated that continued resistance to kanamycin was associated with spontaneous mutations at the 3' end of the 16S rRNA gene (A to G at nt 1420). No mutations were evident in ribosomal protein S12 gene that could have been an alternative target for kanamycin resistance. These ten isolates were then tested for $H_2$ production in liquid culture and one of them exhibited levels that exceeded those of the wild type. This isolate was named Tma200.

Example 9—Metabolite Analysis of Tma100 and Tma200

Figure 3:
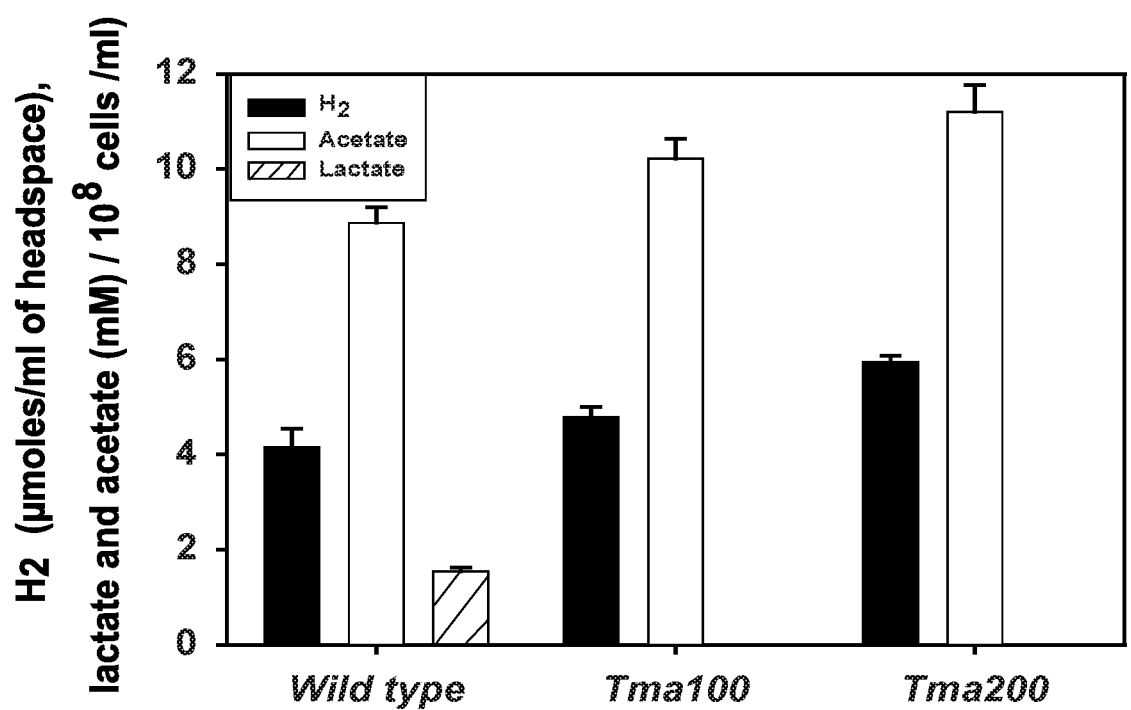
FIG. 3 is a graph showing the comparison of metabolites ($H_2$ and organic acids) of wild type, Tma100 and Tma200 in batch culture. Hydrogen and organic acid production was normalized to $10^8$ cell/mL for all three strains. Error bar represents the standard deviations from biological replicates.

Metabolite analysis was conducted first using small batch cultures after a single growth cycle at 80° C. for 20 hours. Since the wild-type (*T. maritima*) grew to a higher cell density than Tma100 and Tma200 during this time period, the concentration of excreted metabolites ($H_2$, lactic acid and acetic acid) were normalized to cell number (FIG. 3). On this basis, levels of $H_2$ were higher for Tma100 and Tma200 than the wild type by 14.96% and 43% respectively while the other derivatives of Tma100 were not significantly different (data not shown). In addition, acetate levels were higher in Tma100 and Tma200 relative to the wild type by 15.19% and 26.22%, respectively. In contrast, the level of lactate was below the detection limit for both Tma100 and Tma200 while in the wild type it was 1.53±0.08 mM.

Figure 4B:
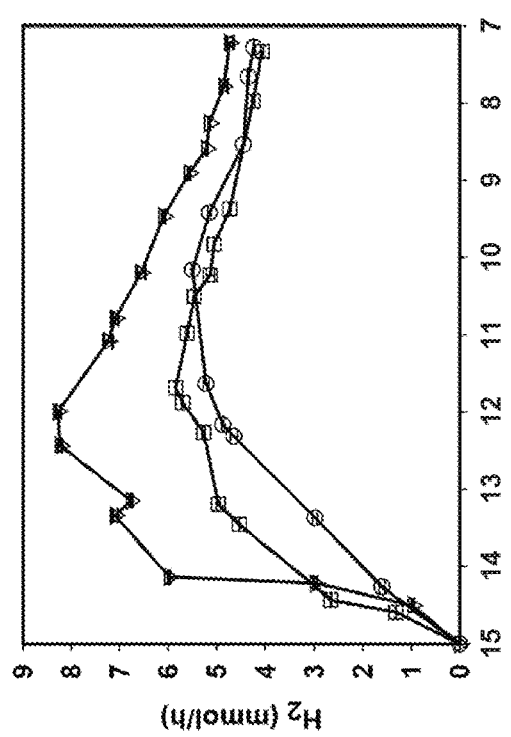
FIG. 4B is a graph showing the comparison of $H_2$ produced (cumulative) by wild type, Tma100 and Tma200 in growth phase.
Figure 4D:
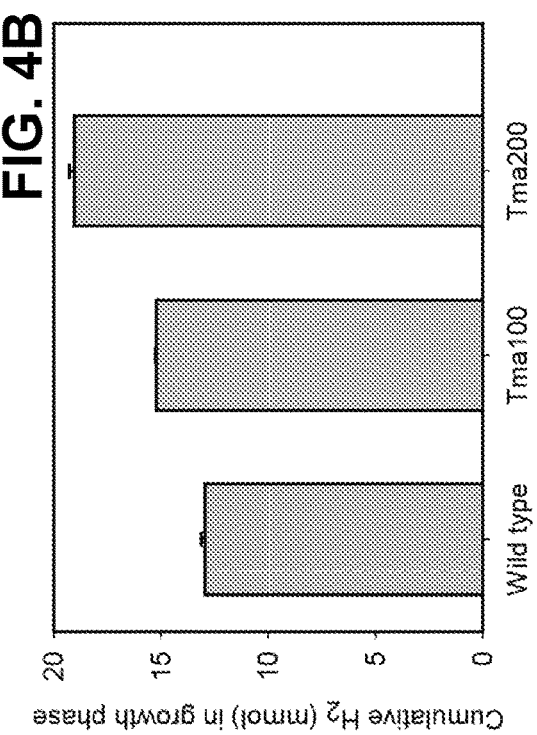
FIG. 4D is a graph showing a relationship between $H_2$ production rate and maltose utilization in wild type (○), Tma100 (□) and Tma200 (∇). Error bar represents the standard deviations from a triplicate analysis.
Figure 4A:
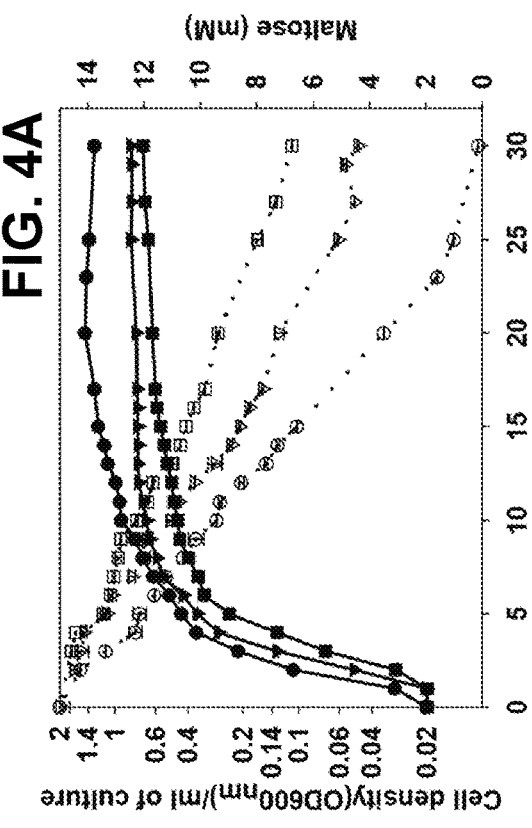
FIG. 4A is a graph showing a relationship between growth (filled symbols; wild type (●), Tma100 (■) and Tma200 (▼)) and maltose utilization (open symbols; wild type (○), Tma100 (□) and Tma200 (∇)).
Figure 4C:
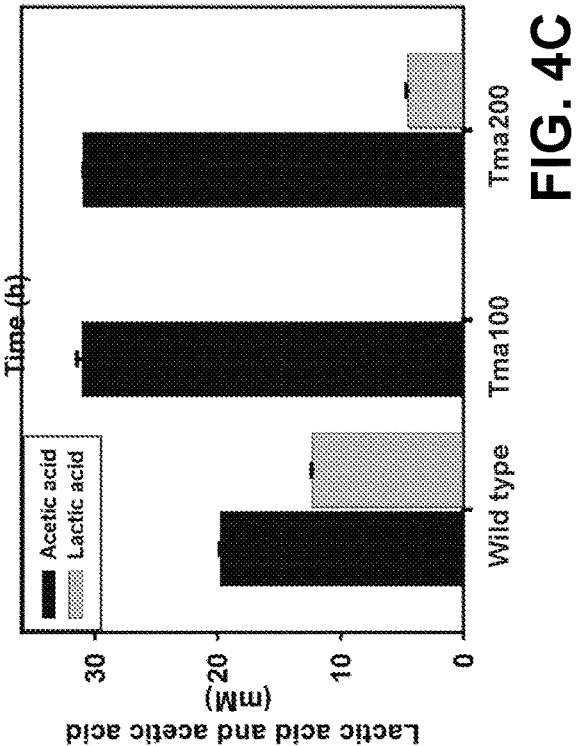
FIG. 4C is a graph showing normalized organic acids (lactate and acetate) of Tma100 and Tma200 to wild type biomass produced in 30 hr.

To determine if $H_2$ accumulation played a role in this process, additional studies were conducted using bioreactors (1.5 L) that enabled $H_2$ removal by head space exchange with $N_2$. Under these conditions, the wild type still grew the fastest and had the highest cell yield followed by Tma200 and then Tma100 (Table 2, FIG. 4A). In contrast, maltose consumption was greatly reduced in Tma100 and Tma200 revealing a defect in catabolism of this sugar. $H_2$ levels produced by Tma100 and Tma200 during exponential growth remained higher relative to the wild type strain by 18% and 49% respectively (FIG. 4B). Acetate levels (after 30 hr) also were higher for both Tma100 (56%) and Tma200 (55%) relative to the wild type, while lactate production by Tma100 was undetectable and reduced by 75% for Tma200 (FIG. 4C). Rather than an effect mediated by elevated $H_2$ production, these data indicated that in the derived strains, the efficiency of fermentation of maltose had increased resulting in elevated levels of $H_2$ on a per cell basis (FIG. 4D, Table 3).

TABLE 2

Growth, Cell Yield and Metabolites During Exponential Growth in Bioreactors

| | Wild type | Tma100 | Tma200 |
| --- | --- | --- | --- |
| Generation time (min) | 53.06 | 88.00 | 63.91 |
| Biomass in growth phase (g cdw/l) | 0.09 ± 0.00 | 0.05 ± 0.00 | 0.07 ± 0.00 |
| H2 produced in growth phase (mmol/l) | 9.40 ± 0.03 | 6.05 ± 0.00 | 11.35 ± 0.07 |
| H2 production per g cdw in growth phase (mmol/g cdw) | 108.12 ± 0.95 | 127.21 ± 0.26 | 159.44 ± 0.99 |

Parameters were obtained from fermenter level studies; Growth phase (0-5 h); cdw, cell dry weight

TABLE 3

Yield Coefficients

| | Wild type | Tma100 | Tma200 |
| --- | --- | --- | --- |
| [a]YH2/maltose | 4.99 ± 0.954 | 5.88 ± 0.357 | 10.28 ± 0.658 |
| [b]YH2/maltose | 5.18 ± 0.006 | 10.74 ± 0.040 | 11.03 ± 0.029 |
| [b]Yacetate/maltose | 1.32 ± 0.006 | 2.04 ± 0.004 | 1.85 ± 0.005 |
| [b]Ylactate/maltose | 0.83 ± 0.001 | ND | 0.2758 ± 0.008 |

Fermentation was carried out in a fermenter and yield coefficient (mole/mole) were determined in
[a]Growth phase (5 hour) and
[b]30 hour fermentation run.

Example 10—The Genetic Basis for Altered Fermentation Efficiency

Figure 8A:
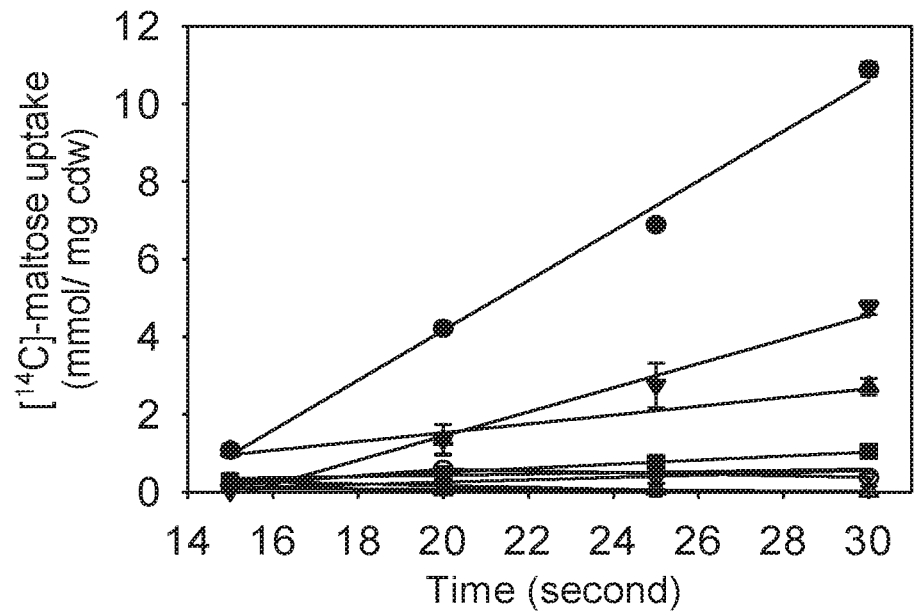
FIG. 8 shows the [$^{14}$C]-maltose uptake kinetics in *T. maritima*, Tma100, Tma200 and Tma300. Panel A represents the [$^{14}$C]-maltose uptake rate in Tma, Tma100, Tma200 and Tma300. Panel B represents the kinetic of [$^{14}$C]-maltose uptake in *T. maritima* and Tma200, respectively, with various concentrations (169 nM-1000 nM) of maltose. The data in Panel B, which represents the average of two independent observations, was fitted to the Michaelis-Menten equation. The error bar represents the standard deviation based on two independent observations.
Figure 8B:
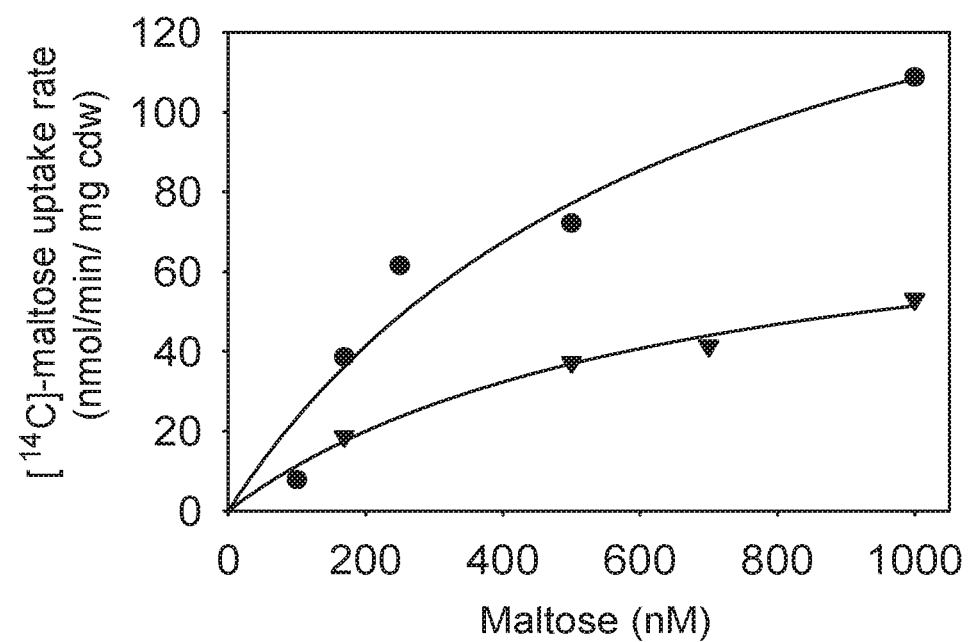

Genome re-sequencing was conducted to identify the genetic basis for $H_2$ overproduction in the derived strains. A tabulated summary of the confirmed mutations with gene annotation, gene/protein length, genome coordinates and proximity to conserved domains is presented (Table 5). Based on genome alignments of the wild type and derived strains, TM1276 (malK) was found to be a genetic hot spot for mutation formation. As two additional malK (TM1232 and TM0421) genes have been annotated in *T. maritima*, TM1276 is designated hereafter as malK-3. In light of the defect in maltose catabolism evident in the derived strains, mutations in TM1276 could play a critical role.

colonies using maltose as compared to cellbiose (FIG. 6). In contrast, Tma200 formed intermediate sized colonies regardless of the type of added sugar. Together with high residual levels of maltose in the bioreactor studies evident with both Tma100 and Tma200 (FIG. 4A), a defect in maltose-related sugar catabolism was evident. Since malK-3 encodes the ATP hydrolyzing subunit of the maltose ABC transporter, the malK-3 mutations could affect maltose uptake. Maltose transport was therefore measured at 75° C. under anaerobic conditions using [$^{14}$C]-maltose (FIG. 8). [$^{14}$C]-maltose uptake was rapid with linear rates of accumulation between 15 and 30 sec after addition. Conversely, maltose uptake in Tma100 remained low. Rates of uptake in nmol/min/mg$_{(cdw)}$ for each strain were; wild type (38.53), Tma200 (18.68), Tma100 (3.13) and Tma201 (6.81) respec-

TABLE 5

Summary of Confirmed Mutations

| Mutant Strain | Substitution/ Deletion | Location of mutation/total length (AA) | Tma ORF Number (annotation as per Nelson et al., 1999, supra) | Gene Annotation |
|---|---|---|---|---|
| Tma100 | A→ G And C → T Synonymous changes | 44$^{th}$ and 49$^{th}$ amino acid | TM1318 | Authentic frameshift/ Putative ATP binding protein of ABC transporter |
| Tma100 | G → A (Gly → Glu) | 148/369 | TM1276 | Maltose/maltodextrin transport ATP-binding protein (MalK) of an ABC transporter |
| Tma100 | G → A (Glu → Lys) | 345/369 | TM1276 | Maltose/maltodextrin transport ATP-binding protein (MalK) of an ABC transporter |
| Tma100 and Tma200 | G → A (Trp → Stop) | 229/614 | TM0460 | Peptide ABC transporter substrate binding protein |
| Tma200 | GT TC (Val Ser) | 233/369 | TM1276 | Maltose/maltodextrin transport ATP-binding protein (MalK) of an ABC transporter |
| Tma200 | G A (Ala Val) | 1045/1690 | TM0459 | RNA polymerase, beta subunit |
| Tma200 | ~10 kb deletion | Deletion from TM1323TM1331 | TM1323-TM1331 | Six hypothetical proteins, two astB/chuR-related protein and two lacI family transcriptional regulator |

Tma100 had a missense mutation (G148E) in malK-3 located in close proximity to the signature motif of the ATP binding domain (FIG. 5). A second mutation (E345L) was located near the C-terminus. In contrast, the malK-3 allele present in Tma200, lacked both G148E and E345L and instead had a mutation located outside the predicted domains (V233S). This same position was also mutated in the other Tma100 derived isolates (Tma201-Tma209) but with a different mutation (V233F) and these strains also lacked the primary mutations identified in Tma100. Tma201 was selected for subsequent experiments.

Example 11—Analysis of malK-3

The role of the malK-3 (Tma1276) mutations on sugar catabolism was examined by comparing colony sizes on plates containing either maltose or cellobiose. While the wild type strain formed large colonies regardless of the supplemented sugar, Tma100 preferentially formed small tively at 169 nM substrate concentration. [$^{14}$C]maltose uptake was significantly reduced by addition of a 100-fold excess of unlabeled maltose (data not shown). The rate of uptake was saturable when wild-type cells were incubated with maltose at concentrations ranging from 100 nM to 1000 nM [$^{14}$C]-maltose. The apparent $K_m$ for wild-type and Tma200 was 680 nM and 649 nM with a $V_{max}$ of 182 and 84.8 nmol/min/mg$_{(cdw)}$, respectively, while kinetic constants for Tma100 could not be determined due to the low rate of uptake.

Part B

Example 12—Strains and Bioreactor

*Thermotoga maritima* MSB8 and excess $H_2$ producing strains (Tma100 and Tma200; see Part A) used in this study were grown in a 3 L double-jacketed glass bioreactors (Applicon, MA) at 80° C. containing 1.5 L complex medium. Bioreactor studies were employed to overcome the growth inhibition caused by $H_2$ accumulation. Prior to inoculation, the cultivation medium was reduced by 0.1% (w/v) $Na_2S$ addition followed by supplementation with maltose at a final concentration of 15 mM. As shown in FIG. 10, anaerobic conditions in the bioreactor were maintained by continuous spurging of $N_2$ at 15 mL/minute. The medium was stirred at 200 rpm using two axial impellers. Temperature, pH and dissolved oxygen were monitored by use of appropriate immersed sensors and a pH of 7 was maintained by metered addition of HCL or NaOH as needed using peristaltic pumps. To minimize water loss, the water vapor present in outgassing headspace was returned to the vessel by condensation using a chilled water supply. Samples were removed periodically using an external syringe to determine culture optical density ($OD_{600}$), and subsequent organic acid and residual maltose was analyzed. For hydrogen sampling, a gas tight syringe (Hamilton) was used to withdraw samples from a rubber septum located on the head plate of the bioreactor.

Example 13—Analysis of Metabolites

Analysis of headspace gas was performed by injecting 500 µL volumes into a gas chromatograph (GC 400 Series, GOWMAC, PA) fitted with a Thermal Conductivity Detector. $N_2$ gas was used as a carrier and separation of the sample gas using a molecular sieve column was carried out at 70° C. The ideal gas law was used to calculate the amount of $H_2$ that was produced at STP. Organic acids and maltose concentrations were determined in culture supernatants by HPLC with comparison to standards. Prior to injection samples were clarified by centrifugation at 10,000×g for 10 min and then filtered (AcroDisc, 0.45 µM). Samples (1 µL) were analyzed using an Agilent 1200 HPLC system and an automated sampler equipped with a Refractive Index Detector and a Hi-Plex H column (ChromTech) operated at 65° C. Isocratic separations used 4 mM sulfuric acid at a rate of 0.4 mL per minute. Aqueous metabolite concentrations were calculated by regression analysis relative to standards. Cell dry weights (cdw) were determined using cell samples from mid-exponential phase cultures.

Example 14—Kinetic Modeling

Mathematica 10.0 package (Wolfram Research Inc, Champaign, Ill.) was used to solve all ordinary differential equations. It was also used for data fitting, for calculating selected parameters with their standard errors, and for performing ANOVA sensitivity analysis.

Example 15—*T. maritima* Growth

The growth of *T. maritima* was modeled assuming cell growth was dependent on first order kinetics:

$$\frac{dX}{dt} = \mu X \quad (1)$$

where X was cellular biomass (g $L^{-1}$), t was time (h), and $\mu(h^{-1})$ was the proportionality constant generally known as the specific growth rate.

The doubling time of the individual cell lines was estimated using the initial condition: $X=2X$ at $t=td$, where td is the doubling time (h). After applying this initial condition, on Eq (1), the following was obtained:

$$td = \frac{0.695}{\mu} \quad (2)$$

Monod's equation (Monod, 1949, Ann. Rev. Microbiol., 3:371-94) or the logistic approach (Luedeking & Piret, 2000, Biotechnol. Bioeng., 67(6):636-44) has been widely used for modeling growth. Here, the logistic approach was used for modeling the growth of *T. maritima* due to its simplicity for calculation of batch fermentation data and the utilization of significant biological and bioreactor geometric parameters. Furthermore, the logistic approach significantly fits the sigmoidal growth profile of *T. maritima* independent of substrate (maltose) concentration.

The logistic model can be presented as:

$$\frac{dX}{dt} = \mu_{max}\left(1 - \frac{X}{X_{max}}\right)X \quad (3)$$

where $\mu_{max}$ is the maximum specific growth rate ($h^{-1}$) and $X_{max}$ is the maximum attainable biomass (g $L^{-1}$).

Applying initial condition $-X=X_0$ at $t=t_0$, the Eq (3) can be simplified to the biomass equation:

$$X = \frac{X_0 X_{max} e^{\mu_{max} t}}{X_{max} - X_0 + X_0 e^{\mu_{max} t}} \quad (4)$$

Example 16—Product Formation

The Leudking-Piret equation (Luedeking & Piret, 2000, supra) was used to model $H_2$ and acetate production, where the rate of product formation was dependent on both growth and non-growth associated production, as shown in following equation:

$$\frac{dP}{dt} = \alpha \frac{dX}{dt} + \beta X \quad (5)$$

where P is the product, i.e., $H_2$ or acetate concentration (mmol $L^{-1}$), a is the growth associated coefficient (mmol $g^{-1}$), and β is the non-growth associated coefficient (mmol $g^{-1}$ h−1).

The product formation can be divided in three different classes (Tevatia et al., 2012, Bioresour. Technol., 119:419-24): (i) Class I, which represents product formation connected to only biomass formation ($\alpha \neq 0$; $\beta = 0$), (ii) Class II, where product formation is moderately connected with biomass formation ($\alpha \neq 0$; $\beta \neq 0$), and (iii) Class III, where product formation is unrelated to biomass formation ($\alpha = 0$; $\beta \neq 0$). The experimental data and model fitting show that $H_2$ and acetate formation by *T. maritima* fall into a Class II category.

Example 17—Maltose Consumption

The maltose consumption equation can be represented by its utilization in biomass formation, maintenance, and product formation:

$$-\frac{dS}{dt} = \frac{1}{Y_{X/S}}\frac{dX}{dt} + mX + \frac{1}{Y_{P/S}}\frac{dP}{dt} \qquad (6)$$

where S is the substrate concentration (mmol L$^{-1}$), $Y_{X/S}$ is the biomass yield coefficient (g-biomass mmol-maltose-1), m is the maintenance coefficient (mmol g$^{-1}$ h$^{-1}$), and $Y_{P/S}$ is the product yield coefficient (g-Biomass mmol-Maltose$^{-1}$).

The H$_2$ and acetate production in *T. maritima* can be related to biomass using the expression: $Y_{P/X}$=−dP(t)/dX(t), where $Y_{P/X}$ is the biomass based product yield.

Example 18—Sensitivity Analysis

The parameters obtained from the modeling of biomass (td, $\mu_{max}$, $X_{max}$), H$_2$ production ($\alpha_{H2}$, $Y_{H2/S}$), acetate production ($\alpha_A$, $\beta_A$, $Y_{A/S}$), and substrate consumption (m, $Y_{X/S}$) were calibrated and analyzed using ANOVA sensitivity analysis. Apart from t-statistic, Pvalue, and R$^2$ values, the data were subjected to analysis with fit residuals and estimated variance.

Example 19—Simulation of Continuous H$_2$ Production

Continuous H$_2$ production was simulated assuming use of a continuous stirred tank reactor (CSTR) that was maintained in a manner consistent with the experimental conditions. The assumptions used for continuous culture simulation included (i) the inflow stream to CSTR had a maltose concentration of 15 mM with no biomass, (ii) the inflow and outflow were set to the same flow rate, and (iii) the respective calculated batch parameters for the three cell lines were assumed to be the same in the experimental conditions. The following equations were used for representing the growth, maltose consumption, and product formation (H$_2$ and acetate):

$$\frac{dX}{dt} = -DX + \mu X \qquad (7)$$

$$\frac{dS}{dt} = D(S_0 - S) - \left(\frac{1}{Y_{X/S}}\frac{dX}{dt} + m_S X + \frac{1}{Y_{P/S}}\frac{dP}{dT}\right) \qquad (8)$$

$$P = Y_{P/X} X \qquad (9)$$

where D was the dilution rate (h$^{-1}$), and S$_0$ was the initial substrate amount (g L$^{-1}$).

Example 20—Kinetic Modeling

The kinetic modeling of growth (Eq. 4), H$_2$ production (Eq. 5), acetate (Eq. 5), and maltose utilization (Eq. 6) resulted in best-fit plots as shown in FIG. 11. Various related kinetic parameters are listed in Table 6.

Example 21—Growth Kinetics

Figure 11B:
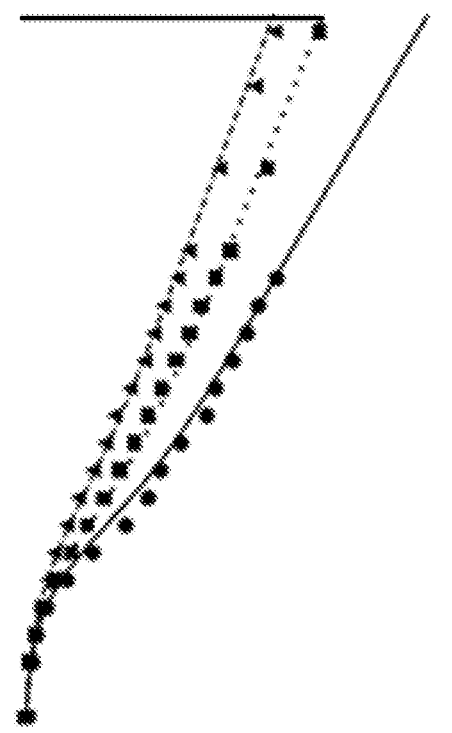
Figure 11A:
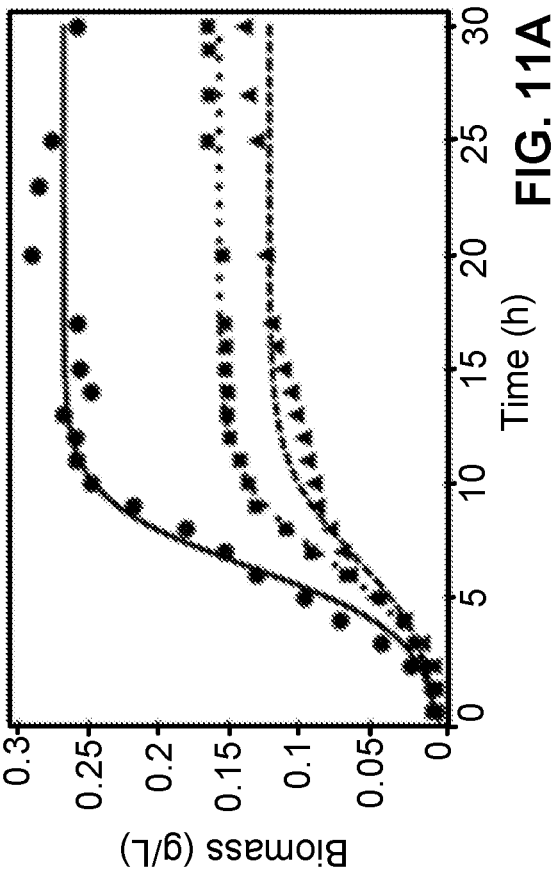
Figure 11D:
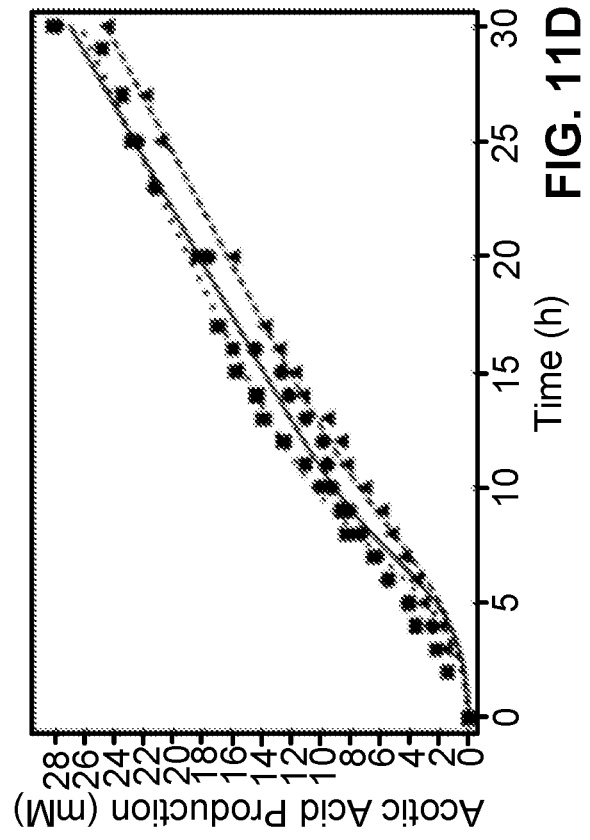

In order to maintain anaerobic conditions and to avoid H$_2$ associated growth inhibition of the cell lines, the headspace of the bioreactor was continuously replaced by supplying nitrogen (N$_2$) at 15 mL/min constant rate throughout the duration of the fermentation. FIG. 11a shows the fitting of the experimental growth data using Eq. (4). The ANOVA analysis (p-values<0.05) and optimal fitting (R$^2$ value of 0.99) of the data confirm the reliability of the model. As evident by the initial slopes of growth curves shown in FIG. 11a, the model fitting demonstrated higher parametric determination of specific growth rates in the wild type followed by Tma200 (~0.75 times lower than wild type) and finally by Tma100 (~0.83 times lower than wild type). These variable growth rates resulted in 0.45 and ~0.59 lower overall biomass in Tma100 and Tma200. The differences in values of the biomass production rates observed between the cell lines were due to variable doubling times and specific growth rates as listed in Table 6 and were independent of H$_2$-associated growth inhibition, since a continuous flow of N$_2$ avoided H$_2$ accumulation. Biomass based productivity of H$_2$ (96 mmol H$_2$/g) in the wild type was comparable with prior fermentation studies (94 mmol/g cdw) carried out with *T. maritima*.

Example 22—Relationships Between Maltose Consumption, Growth and Product Formation The maltose consumption rates, growth and product yields were estimated on the basis of limiting substrate (maltose) utilization during fermentation. The experimental values of maltose consumption in the cell lines were fitted (p<0.05 and R$^2$=0.99) for their respective experimental data points using Eq. (6) (FIG. 11b). The wild type was growing faster (specific growth rate=0.663 h$^{-1}$) and, therefore, utilized more than 95% of the available maltose in 30 h of fermentation. The reduction in the growth rates of Tma100 (0.495 h$^{-1}$) and Tma200 (0.550 h$^{-1}$) were consistent with a slower rate of maltose uptake. The poor growth of Tma100 resulted in a residual amount of unutilized maltose (6.75 mM) in the bioreactor after 30 h of fermentation. Tma200 showed an intermediate growth pattern again resulting in a residual amount of unutilized maltose (4.70 mM). Previously, the genetic and physiological basis was reported for variable maltose consumption and H$_2$ over-production by Tma100 and Tma200 (see Part A) that supports the kinetic parameters determined here for maltose consumption.

In order to determine the amount of substrate utilized for non-growing biomass, the maintenance coefficient was estimated for all three strains (Table 6). The estimated values of the maintenance coefficients show that Tma100 and Tma200 strains were utilizing ~1.37 and ~2.54 times more maltose, respectively, than wild type for their non-growing components that contributed towards the formation of fermentation products.

The proportion of maltose contributing to formation of fermentative products (H$_2$ and acetate) rather than biomass production also determines the overall fermentation productivity; the higher g cdw/maltose in wild type supports this hypothesis (Table 6). This suggests that in the wild type, the maltose consumed results in an excess of biomass formation in deference to formation of fermentative products.

To observe the amount of products (H$_2$ and acetate) synthesized by cell lines (Tma100 and Tma200), the substrate-based product yields were calculated (Table 6). Tma100 and Tma200 were found to be superior in H$_2$ and acetate yields as compared to the wild type. H$_2$ production yields were ~1.56 and ~1.86 times higher, respectively, for Tma100 and Tma200 relative to the wild type, whereas acetate yields were ~1.46 and ~1.58 times higher, respectively.

Figure 11C:
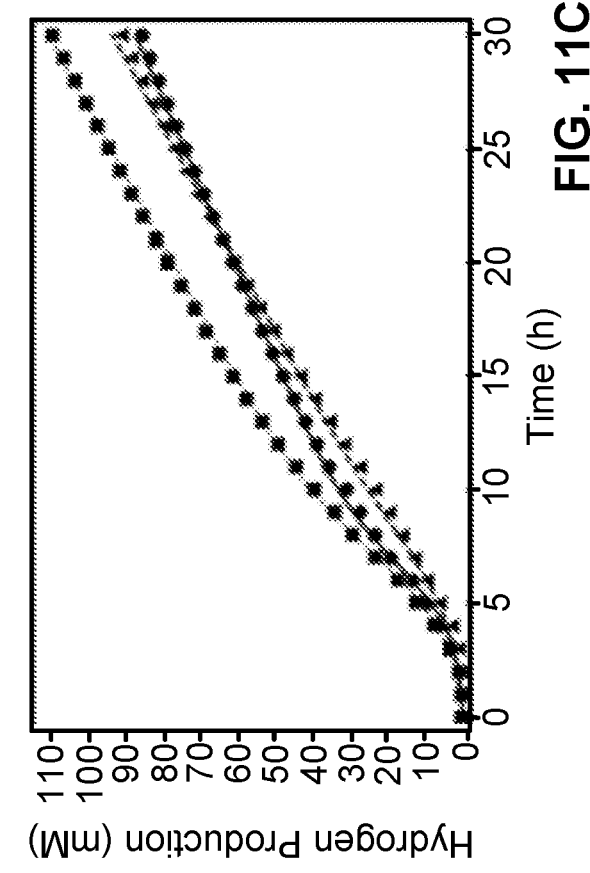

Example 23—Relationship of H$_2$ Production to Kinetic Parameters Determined from Biomass Formation and Maltose Consumption To obtain H$_2$-related kinetic parameters such as an H$_2$ formation coefficient, maximum production, and maximum yield, the experimental data for $H_2$ production for each cell line was fitted using the Leudking-Piret Eq. (5) as shown in FIG. 11c. The fitted values for these parameters are listed in Table 6. The statistical analysis ($p<0.05$) and model fitting ($R^2=0.99$) verify higher confidence of the predictions. It was observed that $H_2$ formation coefficient ($\alpha$), that represents the growth-associated $H_2$ production remained ~1.53 and ~2.26 times higher for Tma100 and Tma200 relative to the wild type, respectively. This highlights that $H_2$ formation is growth dependent and this dependence is much stronger in Tma100 and Tma200, even though their growth rates are lower than that of the wild type. This could mean that production of $H_2$ in Tma100 and Tma200 is higher on a per cell basis. $H_2$ production in the stationary phase is represented by $\beta$, which is the non-growth hydrogen coefficient. A comparatively low value of $\beta$ for wild type than that for Tma100 and Tma200 suggests that $H_2$ production remains lower in the wild type under non-growth conditions, while Tma100 and Tma200 constantly produce $H_2$ even under non-growth conditions. This underscores the unique capacity of Tma100 and Tma200 to produce $H_2$ concomitantly with slow biomass production. To determine the $H_2$ production per unit biomass, the respective exponential growth phase values of $H_2$ were linearly regressed (FIG. 12). The slopes represented the $H_2$ production per mg-cdw. A 2- and 1.6-fold higher slope of $H_2$ production for Tma200 and Tma100, respectively, relative to the wild type was also consistent with a higher $H_2$ productivity per unit biomass. The intercept, representing the minimum concentration of biomass (on a cdw basis) that evolved $H_2$ and was found to be twice as high for Tma200 (1.56 mg $L^{-1}$), relative to those of both the wild type (0.84 mg $L^{-1}$) and Tma100 (0.78 mg $L^{-1}$). Therefore, from the results presented here, it is evident that a lower quantity of biomass and corresponding growth resulted in $H_2$ overproduction by Tma100 and Tma200. This is consistent with prior studies in other organisms where reducing the substrate feeding to decrease biomass resulted in higher $H_2$ production. As reported previously, the differential growth pattern observed for wild type, Tma100 and Tma200 was a result of their respective ability to consume maltose (see Part A). Based on the modeling reported here, $H_2$ production is a function of both growth and maltose utilization. While Tma100 and Tma200 both grew more slowly, relative to the wild type, arising from consumption of less maltose, the $H_2$ productivity was highest for Tma200.

Example 24—A Kinetic Explanation for the Maximum Molar Yield of $H_2$

The most interesting outcome from studies using Tma100 and Tma200 was that $H_2$ production per g cdw increased relative to the wild type, and molar yield of $H_2$ surpassed the biological limit of 4 mole of $H_2$ per hexose (Thauer et al., 1977, Bacteriol. Rev., 41(1):100-80). For Tma100, the ratio of moles of $H_2$/mole of maltose was 9.69±0.20 and, for Tma200, the ratio was 11.54±0.22.

Higher values of growth and non-growth $H_2$ coefficients suggest that $H_2$ production from Tma100 and Tma200 is a continuous process. This could explain the higher molar yield of $H_2$. Furthermore, the maintenance energy coefficient, a physiological parameter that specifies the amount of energy cells require for maintaining homeostasis in the absence of growth (Pirt, 1965, Proc. R. Soc. Lond. B. Biol. Sci., 163(991):224-31), was found to be twice as high for Tma100 and three times higher for Tma200 relative to that of the wild type. This suggests that energy from maltose catabolism is used to maintain the cellular integrity of Tma100 and Tma200 instead of for cellular multiplication.

Physiologically, a metabolic shift towards acetate seems to be another plausible reason for the increased $H_2$ molar yield by Tma100 and Tma200. In the absence of any detectable ethanol production and reduced quantity of lactate formation (none for Tma100 and a 75% reduction for Tma200, relative to the wild type), metabolism may be redirected. A metabolic shift has been observed in different knockout mutants of other organisms, however, in the present study, this metabolic shift seems to occur as a result of variable maltose uptake and growth in Tma100 and Tma200. Prediction of the molar yield of acetate and a non-growth associated coefficient by Leudking-Piret equation verified the metabolic shift in Tma100 and Tma200 (Table 6).

Example 25—Acetic Acid Production and Kinetic Parameters

In a fermentative $H_2$ producing organism, organic acid excretion can determine the effectiveness of $H_2$ production. A metabolic shift towards lactate production decreased the $H_2$ production rate, whereas an increase in acetate improved the $H_2$ production rate. As no lactate was produced by Tma100, whereas a reduction of 75% of lactate was observed in Tma200 (see Part A), only the experimental data for acetate formation was modeled. Previously, in small batch culture studies, the molar yield of acetate has been reported to be 2 moles/glucose in *T. maritima*. However using a larger scale of batch culture, a lower yield of 1 mole acetate per mole of glucose was evident. Furthermore, in a chemostat study of *Pyrococcus furiosus*, a yield of 1.27 mole of acetate per mole of glucose was reported. This suggested that the theoretical 2 mole of acetate per mole of glucose may not be achieved using a larger batch cultivation scale. However, here, the acetate molar yield was estimated to be 0.90 mole per mole of glucose (1.82±0.02 mol/maltose), which is comparative to prior larger scale batch culture studies. Additionally, a lower theoretical molar yield of acetate could result from a loss of carbon, as L-alanine excretion as has been reported previously in *T. maritima*. Since $H_2$ production was tightly linked to acetate production, a proportional increase in the acetate molar yield was achieved by Tma100 and Tma200. The experimental data and model fitting for acetate production (FIG. 11d) using all three strains showed that acetate was both a growth- and a non-growth-associated product. Table 6 lists the values of $\alpha$ and $\beta$ for acetate production. The growth associated coefficient ($\alpha$) increased 1.96-fold and 2.50-times for Tma100 and Tma200, respectively, relative to the wild type. The values of non-growth associated growth ($\beta$) increased by 2.06-fold and 1.42-fold for Tma100 and Tma200, respectively, relative to the wild type. This suggested that organic acid production was independent of growth, however, the production rate in Tma100 and Tma200 was higher than that of wild type at lower biomass. Biomass-based acetate yield by Tma100 and Tma200 was ~1.98-fold higher than the wild type (Table 6). Carbon recovery was close to 99%, indicating a balanced stoichiometry and indicating that the major carbon source was maltose while other carbon present in yeast extract that had been added to the growth medium did not contribute significantly to fermentation product formation.

Example 26—Simulation of a Continuous Biohydrogen Production System: Growth Simulation in a Fermenter Kinetic modeling provides a comprehensive analysis of experimental data to predict operating conditions (Mu et al., 2006, Bioresour. Technol., 97(11):1302-7) that are required for continuous fermentation. Continuous culture studies are crucial to achieve a more stable and higher degree of productivity. Since $H_2$ is mostly a growth dependent product, a continuous stirred tank reactor (CSTR) may be the best choice for continuous $H_2$ production. Here, kinetic modeling of the bioreactor-based experimental data was used to estimate various kinetic parameters to define $H_2$-specific attributes necessary for excess $H_2$ producing strains. These became the basis for simulating a continuous $H_2$ production system. The dilution rate (D) is an important factor that maintains cultivated organisms in their most productive phase, leading to stabilization of the continuous culture-based system. To predict a stable system for $H_2$ production, previously determined kinetic parameters were employed to simulate a continuous stirred tank reactor. For the simulation of continuous $H_2$ production, Eqs. (7)-(9) were solved using the parameters for the respective strains as listed in Table 6. The comparative simulation results for all the cell lines at three different dilution rates are presented in FIG. 13. A lower dilution rate (0.01 $h^{-1}$) maintained a majority of the biomass (~119.6, 118.8, and 118.6 mg/L for wild type, Tma200 and Tma100, respectively) compared to the dilution rate of 0.1 $h^{-1}$ (~100.6, 100.0, and 109.6 mg/L for wild type, Tma200 and Tma100, respectively). Both lower rates (0.01 and 0.1 $h^{-1}$) are likely to maintain a steady state after 5 hr until the end of the fermentation. A higher dilution rate (1 $h^{-1}$) would result in loss of significant biomass. The loss of biomass at a higher dilution rate can be attributed to the higher dilution rate (D) that approached the value of $\mu_{max}$ (Table 6). Consequently, at a higher dilution rate, the continuous culture system is predicted to become unstable due to wash-out of the biomass.

Example 27—Simulation of a Continuous Biohydrogen Production System: Maltose Consumption Simulation During Continuous Cultivation The effect of dilution rate on maltose consumption was estimated at three dilution rates. At a lower dilution rate, due to the presence of a higher number of cells in the bioreactor, excess substrate utilization was likely. From a simulation plot of maltose consumption, it was evident that a lower dilution rate (0.01 $h^{-1}$) would result in rapid utilization of maltose in the wild type with a slower rate of consumption by Tma100 and Tma200. Therefore, the inherent ability of Tma100 and Tma200 to utilize less maltose makes them more economic with respect to substrate utilization. Since bioreactor washout is predicted to occur at 1.0 $h^{-1}$, no maltose utilization would take place even in the presence of 15 mM maltose.

Example 28-Simulation of a Continuous Biohydrogen Production System: $H_2$ Production Simulation in a Fermenter At lower dilution rate (0.01 $h^{-1}$), $H_2$ production would remain constant without any fluctuation and the $H_2$ production rate would be significantly higher in Tma100 and Tma200 relative to that of the wild type. At an intermediate flow rate (0.1 $h^{-1}$), $H_2$ production would fluctuate and would collapse at 1 $h^{-1}$ due to washout of cells. This suggested that maintaining a flow rate of 0.01 $h^{-1}$ would retain the optimum number of cells of Tma100 (118.6 mg/L) and Tma200 (118.8 mg/L), thereby allowing them to produce more $H_2$ than the wild type at a reduced rate of maltose utilization. From this observation, it is reasonable to conclude that maintaining the lower biomass of the wild type (equivalent to Tma100 and Tma200) could improve $H_2$ production by the wild type organism. However, as the only way to maintain a lower biomass of the wild type would be to increase the flow rate, from the simulation, it is evident that an increase in flow rate will decrease $H_2$ production, even though, at the steady state, the biomass of the wild type will become equivalent to strains Tma100 or Tma200. This supports the notion that the $H_2$ production from Tma100 and Tma200 is higher on a per cell basis and will remain higher than that of wild type under any kinetic conditions.

TABLE 6

Fitted values of estimated parameters

| Parameters | *Thermotoga maritima* strains | | |
|---|---|---|---|
| | Wild type | Tma100 | Tma200 |
| (i) Biomass | | | |
| Doubling time, $t_d$ (h) | 1.05 | 1.40 | 1.26 |
| Maximum specific growth, $\mu_{max}$ (1/h) | 0.663 ± 0.017 | 0.495 ± 0.022 | 0.550 ± 0.008 |
| Maximum biomass, $X_{max}$ (g/L) | 0.267 ± 0.004 | 0.121 ± 0.003 | 0.157 ± 0.001 |
| $R^2$ | 0.9961 | 0.9893 | 0.9988 |
| (ii) $H_2$ Production | | | |
| $H_2$ formation coefficient, $\alpha$ (mol-$H_2$/gbiomass) | 0.096 ± 0.01 | 0.147 ± 0.04 | 0.217 ± 0.02 |
| $H_2$ non- growth associated coefficient, $\beta$ (mol-$H_2$/(g-biomass * h)) | 0.09 ± 0.001 | 0.027 ± 0.003 | 0.147 ± 0.041 |
| Maximum $H_2$ production (% cdw) | 4.30 | 7.96 | 10.20 |
| Biomass based hydrogen yield, $Y_{H2/X}$ (mol$H_2$/g-biomass) | 0.204 ± 0.012 | 0.435 ± 0.023 | 0.471 ± 0.024 |
| $R^2$ | 0.9998 | 0.9997 | 0.9999 |
| (iii) Acetate (A) Production | | | |
| A formation coefficient, $\alpha$ (mol-A/g-biomass) | 0.024 ± 0.021 | 0.047 ± 0.025 | 0.060 ± 0.02 |
| A non- growth associated coefficient, $\beta$ (mol-A/(g-biomass * h)) | 0.033 ± 0.002 | 0.068 ± 0.002 | 0.047 ± 0.002 |
| Biomass based A yield, $Y_{A/X}$ (mol-A/gbiomass) | 0.059 ± 0.015 | 0.112 ± 0.026 | 0.117 ± 0.031 |

TABLE 6-continued

Fitted values of estimated parameters

| Parameters | Thermotoga maritima strains | | |
|---|---|---|---|
| | Wild type | Tma100 | Tma200 |
| $R^2$ | 0.9944 | 0.9981 | 0.9971 |
| (iv) Maltose Consumption | | | |
| Maximum biomass yield, $Y_{X/S}$ (gbiomass/mol-maltose) | 30.4 ± 1.05 | 22.3 ± 0.87 | 24.5 ± 0.93 |
| Maintenance coefficient, m (g-biomass/(mol-maltose*h)) | 0.370 ± 0.063 | 0.509 ± 0.084 | 0.940 ± 0.071 |
| Substrate based $H_2$ yield, $Y_{H2/S}$ (mol-H2/molmaltose) | 6.22 ± 0.13 | 9.69 ± 0.20 | 11.54 ± 0.22 |
| Substrate based A yield, $Y_{A/S}$ (mol-A/molmaltose) | 1.82 ± 0.02 | 2.66 ± 0.02 | 2.87 ± 0.02 |
| $R^2$ | 0.9998 | 0.9999 | 0.9999 |
| Ratio ($H_2$/A) | 3.41 | 3.64 | 4.02 |

A—Acetic Acid; $H_2$—Hydrogen gas

Part C

Example 29—Genomic Sequencing of Tma200

*Thermotoga maritima* MSB8 genomovar DSM3109 is a hyperthermophilic anaerobic bacterium that grows at 80° C. producing a maximum of four moles of H2 per mole of glucose (Schroder et al., 1994, Arch. Microbiol., 161:460-70; Selig et al., 1997, Arch. Microbiol., 167:217-32). There are a variety of duplicated genes and direct repeats in its genome, suggesting the potential for genome instability. Genome resequencing of *T. maritima* MSB8 genomovar DSM3109 in 2011 and 2013 (Boucher & Noll, 2011, Appl. Environ. Microbiol., 77:6395-9; Latif et al., 2013, PLoS Genet., 9:e1003485), indicated that the earlier sequenced *T. maritima* MSB8 (NC_000853.1) (Nelson et al., 1999, Nature, 399:323-9) was an evolved laboratory variant with an 8 kb deletion located between TM1847 and TM1848 (annotation according to Nelson et al., 1999, supra)). The 8 kb deletion may have resulted from genome instability. To assess the potential for additional instability, a cell line harboring a chromosomally integrated kanamycin resistant suicide plasmid was allowed to segregate without drug addition but with selection for maltose catabolism as part of ongoing studies involving experimental microbial evolution. The initially sequenced genome of *T. maritima* by Nelson et al. (1999, supra; NC_000853.1) was used to describe the genome changes in the resulting strains. Of 50 clonal isolates screened, 10 underwent deletion formation, including a 10 kb loss between TM1322 and TM1332. One of these 10 kb deletion isolates was named Tma200. The deleted region in Tma200 encoded five hypothetical proteins, two AstB/ChuR-related proteins, one LacI family transcriptional regulator, and three ABC transporter ATP-binding proteins. In addition, two distinct repeat sequences of 920 bp and 313 bp were identified in TM1322 (coordinates; 1340943-1341862 and 1342246-1342558) and TM1332 (1350971-1351890 and 1352274-1352586), respectively. Crossover between the 920 bp direct repeats deleted the intervening region (1341863-1351890). Finally, occurrence of a missense mutation in the beta subunit of DNA polymerase might have increased the likelihood of gene deletion located between TM1322-TM1332 (Saveson & Lovett, 1999, Genetics, 152:5-13; Bzymek & Lovett, 2001, PNAS USA, 98:8319-25).

Genomic DNA was isolated from Tma200 as described previously (Maezato et al., 2011, Methods in Molecular Biology (Clifton, N.J.), 765:435-45). A DNA library was prepared from ~500 bp fragments of randomly sheared genomic DNA. This library was sequenced using an Illumina HiSeq 2000 sequencer and generated 100 bp paired end reads. FASTQ files containing the short reads were mapped to the most recent reference genome of *T. maritima* reported by Latif et al. (2013, supra; NC_021214.1) using Bowtie 2 (v. 2.1.0) and IGV (v 2.3) to locate mutations and deletions that were then verified by DNA sequencing of PCR amplicons. A full consensus genome (1859582 bp) was generated using Samtools (ver. 1.1) and BCFtools alignment processing utilities (ver 1.1) (Li et al., 2009, Bioinformatics, 25:2078-9), using *T. maritima* (NC_021214.1) as a reference.

The genome was annotated using the NCBI Prokaryotic Genome Annotation Pipeline (see ncbi.nlm.nih.gov/genome/annotation_prok/ on the World Wide Web). This pipeline identified 1,918 genes, 1,861 coding DNA sequence (CDS), 7 pseudo-genes, 3 rRNA, 46 tRNA and 7 CRISPR clusters. The complete genome sequence has been deposited in GenBank under the Accession No. CP010967.

Example 30—Demonstration of Correlation Between malK-3 Mutation in Tma200 and Increased Hydrogen Production by Tma200

To clearly demonstrate that the malK-3 mutation encoded by strain Tma200 was responsible for increased hydrogen production, the excess $H_2$ trait was reconstructed in the wild type (uracil auxotroph) strain by replacing the disrupted malK-3 allele of the malK3 mutant with the malK-3 of Tma200. This was accomplished by first creating a malK-3 loss of function disruption mutation by insertion of the groESp::pyrETaf cassette using a uracil auxotroph encoding the pyrE129 mutation as a recipient (FIG. 14A). The malK-3::groESp::pyrETaf mutant was unable to catabolize maltose (FIG. 14B). Maltose catabolism was then repaired using this mutant as a recipient and a PCR amplicon from the Tma200 malK-3 region. This cross could result in two outcomes of either the wild type or the malK-3 allele depending on where recombination occurred relative to the mutations in malK-3 in Tma200. As the cross used a maltose complex medium, all genotypes could form colonies, and the larger colonies encoded a repaired malK-3 allele (either with Tma200 malK3 allele or the wild type allele) and the smaller colonies showed the parental genotype that had the disrupted malK-3 allele (FIG. 14C). In order to distinguish the wild type malK-3 allele from the Tma200 malK-3 allele, the PCR products derived from malK-3 amplification from the larger putative recombinant isolates were subjected to RFLP analysis. The amplicons were digested with AciI, which produces two bands of 675 bp and 963 bp with the malK-3 allele of Tma200 and 21 bp and 1299 bp with the wild type malK-3 allele (FIG. 14D). All five malK-3-repaired isolates were found to possess the malK-3 allele of Tma200. Two of the isolates were verified by sequencing, which showed the malK-3 from Tma200 (FIG. 14E). This experiment was reproduced two times and all repaired isolates had malK-3 from Tma200.

One of the confirmed isolates was further selected for growth physiology and $H_2$ analysis (FIG. 15). The pyrE mutant and the malK-3 mutant were also selected as controls. The Tma200 reconstructed strain showed the pattern of growth and $H_2$ production similar to that of strain Tma200. These findings confirm that the Tma200 allele of malK-3 is necessary and sufficient to increase $H_2$ production by *T. maritima*. This also means that other mutations that arose using the transient gene inactivation method, evident by genomic resequencing of Tma200, had little or no role in the growth physiology and $H_2$ overproduction of this strain.

Part D

Example 31—Acetic Acid Production Simulation in a Fermenter

Similar to $H_2$ production, a proportional amount of acetate will be produced under continuous cultivation conditions, and the overall concentration will be higher than that of the wild type. A higher dilution rate (1 $h^{-1}$) will result in a decrease of acetate due to wash out of acetate producers. This simulation-based prediction resembled results obtained from the experimental batch study (Frascari et al., 2013, Bioresour. Technol., 147:553-61). From the overall simulation, a dilution rate of (0.1 $h^{-1}$) would be suitable for a constant amount of $H_2$ production in the continuous culture. As excess $H_2$ production is an inherent property of Tma100 and Tma200, and the wild type cannot achieve this, even by manipulating cultivation conditions, the derived cell lines are ideal candidates for economic large scale $H_2$ production.

Example 32—Overproduction of Molecular Hydrogen ($H_2$) in Photosynthetic Bacteria The production of hydrogen by photosynthetic bacteria has been studied extensively. While there have been efforts to make mutant cell lines that shift metabolism towards hydrogen production, such efforts have, to date, not succeeded. Transient gene inactivation (TGI) of Rubisco (the first step in the Calvin-Benson cycle) in photoautotrophic bacteria redirects metabolism towards hydrogen production by enhancing availability of reductant. Under photoautotrophic conditions, inactivation of Rubisco is lethal, but shifts consumption of reductant away from carbon reduction. The transient accumulation of reductant leads to mutation of, for example, acetyl-coA synthetase, which normally compensates for the increase in the ATP pool generated via the TCA cycle. This produces evolved cell lines that overproduce hydrogen as a result of uncoupling product formation from biomass synthesis.

Example 33—Overproduction of Ethanol in Ethanol-Producing Microbes by Enhancing Ethanol Toxicity Bioethanol is a clean and sustainable biofuel produced from renewal biomass. Ethanol yields are, however, limited thermodynamically to 2 mol ethanol/mol hexose. For example, mesophilic organisms such as *Saccharomyces cerevisiae* or *Zymomonas mobilis* produce ethanol at yields of approximately 1.9 mol ethanol/mol hexose (Jessen & Orlygsson, 2012, J. Biomed. Biotechnol., 186982), like the hyperthermophiles *Thermoanaerobacter* spp. (*T. ethanolicus*, T. BGIL1), and Caldicellulociruptor bescii (Lacis & Lawford, 1988, Arch. Microbiol., 150:48-55; Lamed & Zeikus, 1980, J. Bacteriol., 144:569-78; Sigurbjornsdottir & Orlygsson, 2012, Applied Energy, 97:785-91; and Taylor et al., 2009, Trends in Biotechnol., 27:398-405).

Transient gene inactivation (TGI) of acetate kinase gene (ackA) or lactate dehydrogenase (ldh) redirects fermentative metabolism towards ethanol production by increasing availability of reductant and, thereby, increasing ethanol yields. This results in an ethanol-based selection and yields mutant cell lines with the traits of higher ethanol yield and higher ethanol tolerance. This also leads to mutations in carbon uptake systems to reduce the metabolic rate and, thereby, promote cell line survival. Cell lines are produced that demonstrate uncoupling of product formation from biomass synthesis.

Example 34—Overproduction of Ethanol in Ethanol Producing Microbes by Enhancing Ethanol Toxicity Transient gene inactivation (TGI) is used to produce strains of *Thermoanaerobacterium saccharolyticum* that overproduce ethanol. This is accomplished by transient inactivation of the *T. saccharolyticum* acetate kinase gene (ackA; Tsac_1745) or lactate dehydrogenase gene (ldh; Tsac_0179). Disruption constructs are produced that encode a 3' terminally truncated ack or ldh in the non-replicating plasmid (pSGD8), which also contains a heat stable kanamycin resistance marker (Shaw et al., 2010, Applied Environ. Microbiol., 76:4713-9). Disruption constructs are introduced into *T. saccharolyticum* using its natural competence for DNA transformation, and cell lines that have undergone recombination at either of these genes (e.g., by single crossover events) are selected.

Briefly, DNA is mixed with cells, which then are allowed to recover for 18 hr in a complex medium. Recombinant cell lines with disrupted ackA or ldh alleles are recovered after plating the DNA-cell mixture onto culture plates containing 200 µg/ml kanamycin and 0.5% cellobiose. Colonies isolated from these selective medium plates then are screened by PCR for the presence of the kanamycin resistance gene and unique fusion joints representing truncated target genes, and unique amplicons are validated by DNA sequencing.

These cell lines then are used to isolate derivatives with increased ethanol production. This is accomplished using at least 25-50 colonies, passaging them on complex medium containing a 5-10 fold lower amount of cellobiose to reduce selective pressure, and on a medium without added kanamycin drug to allow for segregation of the disruption cassette. From this subset of isolates, isolates from each passaged culture are examined by PCR to identify those cell lines in which segregation of the unstable truncated ackA or ldh recombinant intermediate occurred to restore the wild type allele.

Strains that grow slowly on normal amounts of cellobiose then are evaluated for ethanol production. Cell lines that produce ethanol at levels exceeding the wild type strain represent strains in which ethanol production has been metabolically uncoupled from biomass formation. These

Example 35—End Product Toxicity Resulting in Production of Other Value-Added Products Accumulation of some fermentation end-products result in a shift in metabolism that results in production of other by-products. Accumulation of strong growth-inhibiting organic acids such as butyrate or propionate result in increased production of other metabolic by-products such as, for example, lactate, acetate or succinate. Acetate production is favored in *Clostridium butyricum* due to a gain of additional ATP (4ATP) relative to butyric acid synthesis (only 3ATP) per mole of substrate.

Since butyric acid is strongly growth inhibitory, transient gene inactivation (TGI) of genes such as butyraldehyde dehydrogenase, lactate dehydrogenase, or acetaldehyde dehydrogenase/Acetyl CoA transferase, redirects metabolism towards butyrate synthesis and thereby imposes selection pressure to reduce growth and to increase acetate excretion. This also results in compensatory mutations in carbon transport systems that reduce carbon uptake through selection for improved fitness.

Example 36—Transient Gene Inactivation of Simultaneous Targets to Enhance Production Formation Permanent gene disruption is not possible for an essential gene or genes, whereas transient gene inactivation (TGI) temporarily inactivates a gene or genes while inducing a temporary stress response that selects for beneficial mutations. That is, TGI is used to temporarily inactivate multiple essential genes (by concurrent recombination events using discrete selectable genetic markers). This is suitable for biological systems where the ability to produce multiple metabolic end products precludes adequate selective pressure by inactivation of the ability to produce a single end product. For example, *Caldicellulosiruptor bescii* produces the fermentation end products, ethanol, acetate, lactate and hydrogen, and ethanol production is increased by lactate dehydrogenase (ldh) gene inactivation.

Simultaneous inactivation by TGI of acetate kinase (ack) and ldh, or these genes in addition to hydrogenase (hyd), are lethal because it precludes formation of all routes for excretion of excess reductant except ethanol. This generates sufficient selective pressure to force mutation of alternative targets that slow, redirect or uncouple metabolism to produce viable cells and thereby enhanced ethanol production. This approach is applied to organisms such as *Thermoanaerobacter ethanolicus, Thermoanaerobacterium saccharolyticum, Caldicellulosiruptor thermocellum* that harbor relevant metabolic pathways.

Example 37—Overproduction of Commodity Amino Acids

The over-expression of amino acid transport genes lysE (lysine) and thrE in *Corynebacterium glutamicum* led to the overproduction of lysine and threonine. These amino acids have commercial value as commodity food additives. The disruption of either gene via TGI leads to amino acid toxicity in the cells due to loss or a reduction in the export of lysine or threonine from inside the cell. The resulting amino acid toxicity leads to mutation of sugar uptake transporters (e.g., glucose transporters) and, consequently, shift the balance of intracellular reductant to thereby increase the transport of threonine or lysine. Excess intracellular concentrations of these amino acids are toxic because they would impede protein synthesis by enhancing amino acyl tRNA synthetases charging errors, and by promoting feedback inhibition of synthetic pathways. The resulting more-fit cell lines contain compensatory mutations that override the primary targets of lethality to, thereby, enable surviving cells to produce higher levels of excreted amino acids.

Example 38—Simultaneous Sugar Conversion to Hydrogen in *T. maritima*

*T. maritima* consumes many sugars simultaneously, unlike bacteria such as *E. coli* where catabolite repression constrains this process. Reduction in the uptake rate of these sugars at the same time due to mutation and in a manner analogous to maltose as described above enhances the yield of hydrogen production at the expense of biomass formation.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A *Thermotoga maritima* strain comprising at least one mutation in the ATP-binding component of a maltose ABC transporter, wherein the ATP-binding component of the maltose ABC transporter comprises the amino acid sequence of SEQ ID NO:15 and at least one mutation selected from V233S or V233F, wherein the *T. maritima* strain overproduces molecular hydrogen ($H_2$) compared to a *T. maritima* strain lacking the at least one mutation.

2. The strain of claim 1, wherein the strain overproduces acetate compared to a *T. maritima* strain lacking the at least one mutation.

3. The strain of claim 1, wherein the strain produces little to no lactate.

4. The strain of claim 1, wherein the strain further comprises SEQ ID NO:16 having a W229Stop mutation and a deletion of nucleic acid sequences encoding the amino acid sequence of SEQ ID NO:17 and the amino acid sequence of SEQ ID NO:18.

5. A method of increasing the yield of molecular hydrogen ($H_2$) produced by *Thermotoga maritima* in culture, comprising:

inactivating, transiently, the lactate dehydrogenase gene in the *T. maritima* using a selectable marker to produce an inactivated *T. maritima*;

passaging the inactivated *T. maritima* a plurality of times under selective pressure to produce a compensating *T. maritima*, wherein the compensating *T. maritima* comprises a compensating mutation;

screening the compensating *T. maritima* for an increase in $H_2$; and selecting and isolating the compensating *T. maritima* having an increase in $H_2$, wherein the compensating mutation is in the ATP-binding component of a maltose ABC transporter, wherein the ATP-binding component of the maltose ABC transporter comprises the amino acid sequence of SEQ ID NO:15 and at least one mutation selected from V233S or V233F.

6. The method of claim 5, further comprising sequencing the compensating *T. maritima*.

* * * * *

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
```

<223> OTHER INFORMATION: synthetic oligonucleotide

<400> SEQUENCE: 1
atgaaaatag gtatcgtagg actcg                                              25

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
cttggagaaa agccgcagt                                                     19

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 3
gcttcaagcg ccttttatt t                                                   21

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
tcaaaatggt attctcttgc taacg                                              25

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
tcgggcaaga tcccccatgg a                                                  21

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 6
atatgcggtg tgaaataccg ca                                                 22

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
atagtgcccc ttctcatatc                                                    20

<210> SEQ ID NO 8
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 8
ggctaaacta attgaaagtg acaga                                         25

<210> SEQ ID NO 9
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 9
tcgtatgaga actcaacacc ttcagt                                        26

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
gggcgacacg gaaatgtt                                                 18

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
ataataccgc gccacatagc                                               20

<210> SEQ ID NO 12
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 12
cccttttttg cggcattt                                                 18

<210> SEQ ID NO 13
<211> LENGTH: 945
<212> TYPE: DNA
<213> ORGANISM: Artificial Sequence
<220> FEATURE:
<223> OTHER INFORMATION: E. coli GroES chaperonin sequence fused to the
      kanamycin nucleotidyltransferase (HTK)

<400> SEQUENCE: 13
gcttcaagcg cctttttatt tttcttctat ctctttgaat cattgtttat tcattattaa      60
cggtaatgtt ggatttgtgt tgttttttct taatcaatat cccttgaaga ggctcgtaaa    120
aagtagtata tttatattag cagtcgaatg atgagagtgc taaacatcta cgaaggaggg    180
atggatgaag ggacccataa taatgacgag ggaggaaaga atgaaaatag tgcacgagat    240
aaaggagagg atactggaca aatacggaga cgatgtgaag gctatcggag tttacggtag    300

```
cctcggaaga cagaccgatg gaccttactc ggacatagaa atgatgtgtg tgctgagtac    360
tgaaggtgtt gagttctcat acgagtggac aacgggagaa tggaaagcag aggtgaactt    420
ttactctgaa gagatcctcc tggattacgc ctccagagtt gaaccggact ggccactcac    480
ccacggaagg ttcttttcta tcctgcccat atacgatcct ggaggttact cgaaaaagt    540 gtaccagaca gcaaagtccg ttgaggccca gaaattccac gacgctatct gcgcgctgat    600
agtggaagag cttttttgaat acgcgggaaa gtggagaaac ataaggggttc agggaccgac    660 cactttttctg ccatctctta cgtgcaggtt gcgatggcag gtgccatgct catcggactg    720
caccacagga tatgttacac aacgtctgct tccgtgctta ccgaagcggt taagcagccc    780
gatctccccc ctggttacgt gcagctttgc cagctcgtta tgagcggaca gctgtcggac    840
cccgaaaaac ttctcgaatc tcttgagaac ttctggaacg gagtgcagga gtgggcagag    900
agacacggtt acatagtgga cgttagcaag agaataccat tttga                     945
```

<210> SEQ ID NO 14
<211> LENGTH: 936
<212> TYPE: DNA
<213> ORGANISM: Artificial Sequence
<220> FEATURE:
<223> OTHER INFORMATION: E. coli GroES chaperonin sequence fused to the kanamycin nucleotidyltransferase (HTK)

<400> SEQUENCE: 14

```
caagcgcctt tttattttc ttctatctct ttgaatcatt gtttattcat tattaacggt     60
aatgttggat ttgtgtttgt ttttcttaat caatatccct tgaagaggct cgtaaaaagt    120
agtatattta tattagcagt cgaatgatga gagtgctaaa catctacgaa ggagggatgg    180
atgaagggac ccataataat gacgagggag gaaagaatga aaatagtgca cgagataaag    240
gagaggatac tggacaaata cggagacgat gtgaaggcta tcggagttta cggtagcctc    300
ggaagacaga ccgatggacc ttactcggac atagaaatga tgtgtgtgct gagtactgaa    360
ggtgttgagt tctcatacga gtggacaacg ggagaatgga agcagaggt gaacttttac    420 tctgaagaga tcctcctgga ttacgcctcc agagttgaac cggactggcc actcacccac    480
ggaaggttct tttctatcct gcccatatac gatcctggag gttacttcga aaaagtgtac    540
cagacagcaa agtccgttga ggcccagaaa ttccacgacg ctatctgcgc gctgatagtg    600
gaagagcttt ttgaatacgc gggaaagtgg agaaacataa gggttcaggg accgaccact    660
tttctgccat ctcttacgtg caggttgcga tggcaggtgc catgctcatc ggactgcacc    720
acaggatatg ttacacaacg tctgcttccg tgcttaccga agcggttaag cagcccgatc    780 tccccctgg ttacgtgcag ctttgccagc tcgttatgag cggacagctg tcggaccccg    840
aaaaacttct cgaatctctt gagaacttct ggaacggagt gcaggagtgg gcagagagac    900
acggttacat agtggacgtt agcaagagaa taccat                               936
```

<210> SEQ ID NO 15
<211> LENGTH: 369
<212> TYPE: PRT
<213> ORGANISM: Thermotoga maritima

<400> SEQUENCE: 15

```
Met Arg Met Ala Gln Val Val Leu Glu Asn Val Thr Lys Val Tyr Glu
1               5                   10                  15

Asn Lys Val Val Ala Val Lys Asn Ala Asn Leu Val Val Glu Asp Lys
            20                  25                  30
```

```
Glu Phe Val Val Leu Gly Pro Ser Gly Cys Gly Lys Thr Thr Thr
         35                  40                  45

Leu Arg Met Ile Ala Gly Leu Glu Glu Ile Thr Asp Gly Lys Ile Tyr
 50                  55                  60

Ile Asp Gly Lys Val Val Asn Asp Val Glu Pro Lys Asp Arg Asp Ile
 65                  70                  75                  80

Ala Met Val Phe Gln Asn Tyr Ala Leu Tyr Pro His Met Thr Val Tyr
                 85                  90                  95

Glu Asn Met Ala Phe Gly Leu Lys Leu Arg Lys Tyr Pro Lys Asp Glu
            100                 105                 110

Ile Asp Arg Arg Val Arg Glu Ala Ala Lys Ile Leu Gly Ile Glu Asn
        115                 120                 125

Leu Leu Asp Arg Lys Pro Arg Gln Leu Ser Gly Gly Gln Arg Gln Arg
130                 135                 140

Val Ala Val Gly Arg Ala Ile Val Arg Asn Pro Lys Val Phe Leu Phe
145                 150                 155                 160

Asp Glu Pro Leu Ser Asn Leu Asp Ala Lys Leu Arg Val Gln Met Arg
                165                 170                 175

Ser Glu Leu Lys Lys Leu His His Arg Leu Gln Ala Thr Ile Ile Tyr
            180                 185                 190

Val Thr His Asp Gln Val Glu Ala Met Thr Met Ala Asp Lys Ile Val
        195                 200                 205

Val Met Lys Asp Gly Glu Ile Gln Gln Ile Gly Thr Pro His Glu Ile
210                 215                 220

Tyr Asn Ser Pro Ala Asn Val Phe Val Ala Gly Phe Ile Gly Ser Pro
225                 230                 235                 240

Pro Met Asn Phe Val Asn Ala Arg Val Val Arg Gly Glu Gly Gly Leu
                245                 250                 255

Trp Ile Gln Ala Ser Gly Phe Lys Val Lys Val Pro Lys Glu Phe Glu
            260                 265                 270

Asp Lys Leu Ala Asn Tyr Ile Asp Lys Glu Ile Ile Phe Gly Ile Arg
        275                 280                 285

Pro Glu Asp Ile Tyr Asp Lys Leu Phe Ala Leu Ala Pro Ser Pro Glu
290                 295                 300

Asn Thr Ile Thr Gly Val Val Asp Val Val Glu Pro Leu Gly Ser Glu
305                 310                 315                 320

Thr Ile Leu His Val Lys Val Gly Asp Asp Leu Ile Val Ala Ser Val
                325                 330                 335

Asn Pro Arg Thr Gln Ala Lys Glu Glu Gln Lys Ile Asp Leu Val Leu
            340                 345                 350

Asp Met Thr Arg Met His Ala Phe Asp Lys Glu Thr Glu Lys Ala Ile
        355                 360                 365

Ile

<210> SEQ ID NO 16
<211> LENGTH: 614
<212> TYPE: PRT
<213> ORGANISM: Thermotoga maritima

<400> SEQUENCE: 16

Met Lys Lys Leu Phe Val Leu Phe Leu Ala Val Leu Ser Val Leu Val
 1               5                  10                  15

Leu Ala Glu Val Lys Asn Pro Asp Thr Ile Ile Asp Ala Thr Ile Gly
             20                  25                  30
```

```
Glu Pro Asp Thr Leu Asp Pro His Phe Ala Tyr Asp Thr Ala Ser Gly
            35                  40                  45

Glu Val Ile Tyr Asn Val Tyr Glu Asn Leu Ile Ala Tyr Lys Gly Glu
     50                  55                  60

Ser Leu Thr Glu Phe Glu Pro Arg Leu Ala Glu Arg Trp Glu Ile Leu
 65              70                  75                      80

Asp Asp Gly Lys Thr Tyr Lys Phe Tyr Ile Arg Lys Gly Val Lys Phe
                 85                  90                  95

His Glu Gly Gly Asp Leu Thr Pro Glu Asp Val Glu Tyr Ser Phe Glu
                100                 105                 110

Arg Gly Leu Ile Phe Asp Pro Thr Ala Gly Pro Met Trp Met Leu Trp
            115                 120                 125

Glu Ala Leu Phe Gly Val Asp Ser Leu Glu Thr Phe Val Glu Glu Lys
            130                 135                 140

Ile Gly Lys Pro Tyr Ser Glu Leu Phe Asp Glu Asn Gly Glu Pro Leu
145                 150                 155                 160

Pro Glu Tyr Arg Asp Ala Leu Ile Lys Ile Tyr Thr Asp Tyr Ile Asp
                165                 170                 175

Pro Ala Ile Glu Val Glu Gly Asp Ala Val Phe His Leu Val Arg
                180                 185                 190

Pro Phe Ala Pro Phe Met Tyr Ile Leu Ala Gln Ser Ala Ser Trp Ser
            195                 200                 205

Ala Val Leu Asp Lys Glu Trp Cys Ile Glu Ile Gly Cys Trp Asp Gly
            210                 215                 220

Arg Ala Asp Thr Trp Trp Lys Tyr His Asp Ile Arg Lys Glu Asp Ser
225                 230                 235                 240

Pro Leu Tyr Ala Arg Met Asn Gly Thr Gly Pro Phe Lys Phe Val Glu
                245                 250                 255

Trp Asp Arg Ala Gln Gln Lys Val Ile Leu Glu Arg Asn Asp Asn Tyr
            260                 265                 270

Trp Arg Glu Pro Ala Lys Ile Lys Arg Val Ile Ile Trp Gly Ile Asp
            275                 280                 285

Glu Trp Ser Thr Arg Arg Ala Met Phe Leu Gln Gly Asp Ala Asp Ile
            290                 295                 300

Cys Ala Val Pro Thr Gln Tyr Leu Glu Gln Val Glu Gly Lys Pro Gly
305                 310                 315                 320

Val Thr Val Val Lys Gly Leu Pro Glu Leu Ala Val Thr Ser Leu His
                325                 330                 335

Phe Ala Trp Asn Val Pro Glu Asp Ser Lys Tyr Ile Gly Ser Gly Lys
            340                 345                 350

Leu Asp Gly Asn Gly Ile Pro Pro Asp Phe Phe Ser Asp Glu Asn Val
            355                 360                 365

Arg Lys Ala Phe Ile Tyr Ala Phe Asp Tyr Asp Thr Phe Ile Asn Glu
            370                 375                 380

Val Leu Lys Gly Leu Gly Arg Lys Ile Pro Thr Asp Leu Pro Glu Gly
385                 390                 395                 400

Leu Leu Gly Phe Asn Glu Glu Leu Leu Asn Asp Pro Asp Ala Pro His
            405                 410                 415

Phe Asp Ile Val Lys Ala Thr Glu Tyr Phe Lys Lys Ala Trp Asn Gly
            420                 425                 430

Glu Val Trp Lys Lys Gly Phe Lys Ile Thr Leu Leu Tyr Asn Thr Gly
            435                 440                 445
```

```
Asn Glu Val Arg Arg Gln Ala Ala Glu Met Leu Lys Ala Tyr Ile Glu
    450                 455                 460

Met Ile Asn Pro Lys Phe Lys Val Glu Val Arg Gly Val Gln Trp Pro
465                 470                 475                 480

Thr Tyr Leu Asp Ala Thr Lys Arg Gly Glu Val Pro Ala Phe Ile Ile
                485                 490                 495

Gly Trp Leu Ala Asp Tyr Pro Asp Pro His Asn Phe Ile Phe Thr Tyr
                500                 505                 510

Tyr His Ser Ala Gly Val Tyr Ser Gly Arg Gln Gly Glu Asn Phe Arg
                515                 520                 525

Lys Phe Val Ser Thr Pro His Pro Asp Leu Gly Gly Arg Ser Leu Asp
    530                 535                 540

Glu Leu Ile Glu Glu Ala Ile Ala Lys Thr Asp Pro Ala Glu Arg Gln
545                 550                 555                 560

Ala Leu Tyr Glu Glu Ile Gln Arg Phe Ala Met Lys His Ala Leu Gly
                565                 570                 575

Met Pro Leu Tyr Gln Pro Leu Gly Val Arg Val Gln Arg Ser Trp Val
                580                 585                 590

Lys Gly Trp Tyr His Asn Pro Met Arg Pro Gly Asp Asp Tyr Tyr Val
                595                 600                 605

Leu Trp Lys Ala Glu Glu
            610

<210> SEQ ID NO 17
<211> LENGTH: 60
<212> TYPE: PRT
<213> ORGANISM: Thermotoga maritima

<400> SEQUENCE: 17

Met Ile Ile Phe Leu Ile Leu Val Leu Leu Ser Thr Ile Ile Phe Ala
1               5                   10                  15

Asp Lys Val Lys Thr Asp Asn Glu Thr His Ser Trp Lys Ser Glu Ile
                20                  25                  30

Thr Glu Gln Val Gln Val Ala Pro Lys Ser Ala Ala Thr Cys Glu Val
                35                  40                  45

Thr Phe Lys Gly Ser Thr Ala Gly Asn Gln Ser Phe
    50                  55                  60

<210> SEQ ID NO 18
<211> LENGTH: 522
<212> TYPE: PRT
<213> ORGANISM: Thermotoga maritima

<400> SEQUENCE: 18

Met Lys Met Lys Gly Ile Glu Ser Leu Lys Glu Ile Phe Lys Tyr Gly
1               5                   10                  15

Ala Phe Ser Leu Pro Val Ala Asn Tyr Leu Leu Cys Glu Gly Asn Ile
                20                  25                  30

Pro Gly Asp Cys Lys Arg Ile Leu Asp Val Leu Lys Leu Ala Trp Lys
                35                  40                  45

Gly Asn Phe Lys Glu Ala Ile Arg Arg Ala Asp Lys Ala Val Glu Asn
                50                  55                  60

Ser Arg Ser Glu Thr Ala Lys Tyr Phe Leu Leu Ala Asn Lys Leu Val
65                  70                  75                  80

Phe Leu Lys Tyr Thr Gly Lys Val Asp Met Asn Leu Tyr Arg Tyr Leu
                85                  90                  95
```

```
Lys Arg Asn Leu Pro Lys Met Ser Lys Ser Ile Arg Asp Thr Val Ile
                100                 105                 110

Val Thr Leu Ile Asn Phe Glu Ala Ser Gly Val Lys Pro Leu Arg Lys
        115                 120                 125

Met Arg Val Trp Lys Asn Asn Tyr Arg Lys Ser Thr Leu Ser Phe Leu
    130                 135                 140

Tyr Leu Ser Leu Ala Arg Arg Glu Ala Asp Ser Gly Asp Leu Ser Glu
145                 150                 155                 160

Ala Val His Gly Tyr Ile Gln Ala Tyr Lys Leu Ser Arg Glu Ile Pro
                165                 170                 175

His Pro Thr Cys Met Val Ser Ser Leu Asn Asp Leu Ala Trp Asp Ile
            180                 185                 190

Lys Glu Lys His Pro Lys Leu Ala Tyr Asp Leu Ser Lys Gly Ala Val
        195                 200                 205

Phe Trp Leu Gly Tyr Tyr Arg Glu Glu Pro Gly Asn Leu Phe Gly Ala
210                 215                 220

Leu Asp Thr Leu Phe Val Val Glu Lys Asp Met Asp Ser Pro Ser Ile
225                 230                 235                 240

His Ser Thr Ala His Ile Ile Val Ser Leu Pro Val Pro Glu Asp Tyr
                245                 250                 255

Leu Ser Leu Leu Lys Lys Ala Lys Lys Phe Val Leu Asp Tyr Thr Gly
                260                 265                 270

Ser Thr Tyr Pro Asn Thr Ser Gln Leu Arg Arg Tyr Val Glu Lys Val
            275                 280                 285

Ala Trp Lys Gly Lys Thr Leu Ser Ser Lys Gly Ile Ser Asp Ile Leu
        290                 295                 300

Lys Gly Lys Thr Lys Met Ile Arg Ala Asp Thr Ile Arg Lys Leu Leu
305                 310                 315                 320

Thr Ser Gly Val Asp Thr Gly Ala Pro Phe Pro Val Trp Asn Glu Trp
                325                 330                 335

Ile Lys Met Glu Ile Glu Arg Lys Tyr Arg Glu Ser Ser Glu Lys Leu
                340                 345                 350

Lys Glu Leu Pro Phe His Gln Arg Gln Ile Leu Phe Leu Thr Thr Tyr
            355                 360                 365

Met Ala Leu Leu Asp Arg Glu Phe Leu Ser Arg Lys Glu Lys Leu Lys
    370                 375                 380

Lys Ala Tyr Thr Leu Leu Glu Asp Ile Glu Ser Phe Ala Asp Phe Met
385                 390                 395                 400

Ala Lys Asp His Arg Thr Met Glu Phe Val Val Ser Met Val Lys Ala
                405                 410                 415

His Pro Phe Val Glu Gly Arg Lys Glu Ala Val Lys Arg Ala Leu Ala
            420                 425                 430

Arg Met Lys Arg Lys Arg Leu Glu Arg Phe Val Leu Arg Tyr Ile Glu
    435                 440                 445

Met Lys Glu Ser Asp Arg Lys Leu Leu Asp Arg Phe Leu Arg Asn Tyr
450                 455                 460

Gly Arg Tyr Asp Gly Val Arg Phe Gly Ile Arg Leu Lys Gly Pro Glu
465                 470                 475                 480

Val Val Arg Glu Phe Ala Lys Lys Tyr Ser Leu Lys Val Gln Pro Leu
                485                 490                 495

Phe Ala Ala Phe Trp Cys Glu Glu Asp Gly Arg Val Arg Arg Arg Leu
            500                 505                 510
```

```
Glu Arg Ile Leu Lys Tyr Met Phe Leu Asn
        515                 520
```